United States Patent [19]

Kubo et al.

[11] 4,335,129

[45] Jun. 15, 1982

[54] THIAZOLO[3,2-b]ISOQUINOLINES, COMPOSITIONS AND USE THEREOF

[75] Inventors: Kazuo Kubo, Urawa; Noriki Ito, Iwatsuki; Isao Souzu, Urawa; Yasuo Isomura, Yokohama; Hiroshige Homma, Omiyu, all of Japan

[73] Assignee: Yamanouchi Pharmaceutical Co. Ltd., Tokyo, Japan

[21] Appl. No.: 229,183

[22] Filed: Jan. 28, 1981

Related U.S. Application Data

[60] Continuation of Ser. No. 29,000, Apr. 11, 1979, abandoned, which is a division of Ser. No. 861,980, Dec. 19, 1977, Pat. No. 4,163,844.

[30] Foreign Application Priority Data

Dec. 28, 1976 [JP] Japan .................. 51-157867
Oct. 11, 1977 [JP] Japan .................. 52-121666

[51] Int. Cl.³ ............... A61K 31/47; C07D 513/04
[52] U.S. Cl. .......................... 424/258; 424/248.51; 424/250; 544/125; 544/126; 544/361; 546/65; 546/80
[58] Field of Search ............... 544/125, 126, 361; 546/65, 80; 424/248.51, 250, 258

[56] References Cited

FOREIGN PATENT DOCUMENTS 1960376  6/1971  Fed. Rep. of Germany .

*Primary Examiner*—Robert W. Ramsuer
*Attorney, Agent, or Firm*—Burgess, Ryan and Wayne

[57] ABSTRACT

Nitrogen containing heterocyclic compounds shown by the formula

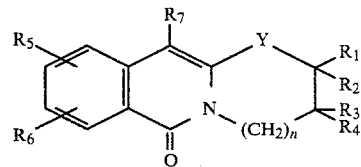

wherein Y represents an oxygen atom, a sulfur atom, or a group shown by

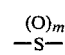

(wherein m is 1 or 2); n represents 0 or 1; $R_1$ and $R_4$, which may be the same or different, each represents a hydrogen atom, a lower alkyl group, or a lower alkenyl group; $R_2$ and $R_3$, which may be the same or different, each represents a hydrogen atom, a hydroxyl group, a lower alkanoyloxy group, a lower alkyl group or a lower alkenyl group; said $R_2$ and $R_3$ may further form together a double bond; $R_5$ and $R_6$, which may be the same or different, each represents by hydrogen atom, a halogen atom, a hydroxyl group, a nitro group, an amino group, a lower alkoxy group, a mono or di lower alkylamino group, or a lower alkyl group; said $R_5$ and $R_6$ may further form together a lower alkylenedioxy group; and $R_7$ represents a hydrogen atom, a halogen atom, a lower alkanoyl group, a phenyl group, a phenyl lower alkyl group, a lower alkyl group, a hydroxy lower alkyl group, a di lower alkylamino lower alkyl group, a pyrrolidino lower alkyl group, a piperidino lower alkyl group, a morpholino lower alkyl group, or a 4-lower alkylpiperazino lower alkyl group;

(1) when said $R_1$, $R_2$, $R_3$, $R_4$, $R_5$, $R_6$ and $R_7$ are hydrogen atom and n is 0, said Y is a group shown by

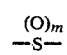

and (2) when said $R_1$, $R_2$, $R_3$, $R_4$ and $R_7$ are hydrogen atom, at least one of said $R_5$ and $R_6$ is the aforesaid group other than hydrogen atom, and n is 0, said Y is oxygen atom or a group shown by

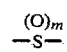

and the pharmacologically acceptable non-toxic salts thereof.

17 Claims, No Drawings

THIAZOLO[3,2-b]ISOQUINOLINES, COMPOSITIONS AND USE THEREOF

This is a continuation of application Ser. No. 29,000, filed Apr. 11, 1979, now abandoned, which is a divisional of U.S. Pat. No. 861,980, filed Dec. 19, 1977, now U.S. Pat. No. 4,163,844 which issued Aug. 7, 1979.

The compounds are strong analgesic anti-inflammatory agents.

DETAILED DESCRIPTION OF THE INVENTION

The present invention relates to novel nitrogen-containing heterocyclic compounds. More particularly, the invention relates to the nitrogen-containing heterocyclic compounds shown by the formula I

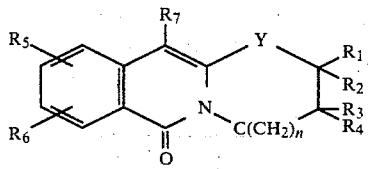

wherein Y represents an oxygen atom, a sulfur atom, or a group shown by

(wherein m is 1 or 2); n represents 0 or 1; $R_1$ and $R_4$, which may be the same or different, each represents a hydrogen atom, a lower alkyl group, or a lower alkenyl group; $R_2$ and $R_3$, which may be the same or different, each represents a hydrogen atom, a hydroxyl group, a lower alkanoyloxy group, a lower alkyl group or a lower alkenyl group; said $R_2$ and $R_3$ may further form together a double bond; $R_5$ and $R_6$, which may be the same or different, each represents a hydrogen atom, a halogen atom, a hydroxyl group, a nitro group, an amino group, a lower alkoxy group, a mono or di lower alkylamino group, or a lower alkyl group; said $R_5$ and $R_6$ may further form together a lower alkylenedioxy group; and $R_7$ represents a hydrogen atom, a halogen atom, a lower alkanoyl group, a phenyl group, a phenyl lower alkyl group, a lower alkyl group, a hydroxy lower alkyl group, a di lower alkylamino lower alkyl group, a pyrrolidino lower alkyl group, a piperidino lower alkyl group, a morpholino lower alkyl group, or a 4-lower alkylpiperazino lower alkyl group;

(1) when said $R_1$, $R_2$, $R_3$, $R_4$, $R_5$, $R_6$ and $R_7$ are hydrogen atom and n is 0, said Y is a group shown by

and (2) when said $R_1$, $R_2$, $R_3$, $R_4$ and $R_7$ are hydrogen atom, at least one of said $R_5$ and $R_6$ is the aforesaid group other than hydrogen atom, and n is 0, said Y is oxygen atom or a group shown by

and the pharmacologically acceptable non-toxic salts thereof.

Since the compounds of this invention shown by the formula I have very strong anti-inflammatory activity and also strong analgesic acitivity, the compounds are used as strong analgesic anti-inflammatory agents.

The definitions of the terms used in the specification and the claims of this invention are as follows:

That is, "lower alkyl group" is a straight or branched chain alkyl group having 1-6 carbon atoms and includes, for example, methyl, ethyl, porpyl, isopropyl, n-butyl, isobutyl, n-butyl, sec-butyl, tert-butyl, amyl, isoamyl, and n-hexyl groups. "Lower alkenyl group" is a straight or branched chain alkenyl group having 2-6 carbon atoms and includes, for example, vinyl, allyl, and 2-butenyl groups. "Lower alkoxy group" is a straight or branched chain alkoxy group having 1-6 carbon atoms and includes, for example, methoxy, ethoxy, propoxy, isopropoxy, n-butoxy, amyloxy, and n-hexyloxy groups. "Lower alkylenedioxy group" is a straight chain alkylenedioxy group having 1-4 carbon atoms and includes, for example, methylenedioxy, ethylenedioxy, and porpylenedioxy groups. "Lower alkanoyl group" is a straight or branched chain alkanoyl group having 1-6 carbon atoms and includes, for example, formyl, acetyl, propionyl, butyryl, and isobutyryl groups. "Halogen atom" includes fluorine, chlorine, bromine, and iodine atoms. And, "phenyl lower alkyl group" is a phenyl-substituted lower alkyl group and includes, for example, benzyl and phenethyl groups.

The compounds of this invention shown by the formula I have a feature of chemical structure in the point that the 2-position and the 3-position of the 1-isoquinolone are cyclized by a hetero-atom (oxygen atom or sulfur atom) and an alkylene group and it has not hitherto been known that such nitrogen-containing heterocyclic compounds have excellent anti-inflammatory activity. In addition, as such nitrogen-containing heterocyclic compounds, 5-oxo-2,3-dihydro-5H-thiazolo[3,2-b]isoquinoline shown by the formula

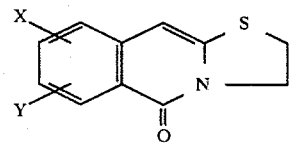

wherein X represents a hydrogen atom, a chlorine atom, a bromine atom, an alkyl group, an alkoxy group, an alkylamino group, a dialkylamino group, an arylamino group, an acylamino group, an aryl group, or an aryloxy group and Y represents a hydrogen atom, a chlorine atom, a bromine atom, an alkyl group or an alkoxy group is disclosed in Offenlegungsschrift 1,960,376 and also 5-oxo-2,3-dihydro-5H-oxazolo[3,2-b]isoquinoline

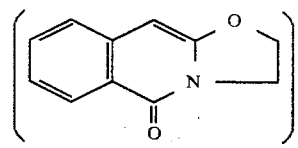

is disclosed in "Ann. Chemie, 729, 83–96(1969)" as intermediates for dyes in both cases. However, there are no descriptions about the usefulness of these compounds as medicaments in the literatures.

The preferred homologues of the compounds of this invention are the nitrogen-containing heterocyclic compounds of furmula I wherein Y is a sulfur atom or the group shown by

and each of R₂ and R₃ is a hydrogen atom or a lower alkyl group. Other preferred homologues of the compounds of this invention are the nitrogen-containing heterocyclic compounds of formula I wherein Y is an oxygen atom and each of R₂ and R₃ is a hydrogen atom or a lower alkyl group.

Examples of the particularly preferred compounds of this invention are
6-oxo-3,4-dihydro-2H,6H-1,3-thiazino[3,2-b]isoquinoline
6-oxo-3,4-dihydro-2H,6H-1,3-thiazino[3,2-b]isoquinoline-1-oxide
6-oxo-3,4-dihydro-2H,6H-1,3-thiazino[3,2-b]isoquinoline-1,1-dioxide
8-chloro-6-oxo-3,4-dihydro-2H,6H-1,3-thiazino[3,2-b]isoquinoline
8-chloro-6-oxo-3,4-dihydro-2H,6H-1,3-thiazino[3,2-b]isoquinoline-1-oxide
7-chloro-5-oxo-2,3-dihydro-5H-thiazolo[3,2-b]isoquinoline-1-oxide
7-chloro-3-methyl-5-oxo-2,3-dihydro-5H-thiazolo[3,2-b]isoquinoline
7-chloro-3-methyl-5-oxo-2,3-dihydro-5H-thiazolo[3,2-b]isoquinoline-1-oxide
7-chloro-5-oxo-2,3-dihydro-5H-oxazolo[2,3-b]isoquinoline
8-chloro-6-oxo-3,4-dihydro-2H,6H-1,3-oxazino[3,2-b]isoquinoline
11-methyl-6-oxo-3,4-dihydro-2H,6H-1,3-thiazino[3,2-b]isoquinoline
11-methyl-6-oxo-3,4-dihydro-2H,6H-1,3-thiazino[3,2-b]isoquinoline-1,1-dioxide and
11-formyl-6-oxo-3,4-dihydro-2H,6H-1,3-thiazino[3,2-b]isoquinoline As the phamacologically acceptable non-toxic salts of the compounds of this invention shown by formula I, there are the addition salts of an acid such as hydrochloric acid, hydrobromic acid, sulfuric acid, nitric acid, phosphoric acid, etc.

The compounds of this invention shown by the formula I can be prepared as follows:

(A). The compound of this invention shown by the formula I wherein Y is an oxygen atom or a sulfur atom and R₂ is a hydrogen atom or a lower alkyl group, that is the compound shown by the formula Ia

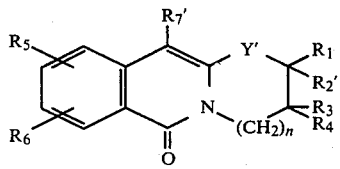

wherein Y' represents an oxygen atom or a sulfur atom; R₂' represents a hydrogen atom, a lower alkyl group, or a lower alkenyl group; R₇' represents a hydrogen atom, a phenyl group, a phenyl lower alkyl group, a lower alkyl group, a di-lower alkylamino lower alkyl group, a pyrrolidino lower alkyl group, a piperidino lower alkyl group, a morpholino lower alkyl group, or a 4-lower alkylpiperazino lower alkyl group; and R₁, R₃, R₄, R₅, R₆ and n have the same significance as in the formula I; (1) when R₁, R₂', R₃, R₄, R₅, R₆ and R₇' are hydrogen atom, n is 1, and (2) when R₁, R₂', R₃, R₄ and R₇' are hydrogen atom, at least one of R₅ and R₆ is the aforesaid group other than hydrogen atom, and n is 0, Y' is oxygen atom can be prepared by reacting the compound shown by the formula II

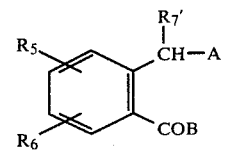

wherein A represents a carboxy group or a cyano group; B represents a hydroxyl group or a lower alkoxy group; and R₅, R₆ and R₇' have the same significance as above; when A is a carboxy group, B is a hydroxyl group with the compound shown by the formula III

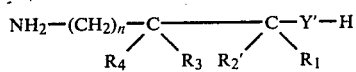

wherein Y', R₁, R₂', R₃, R₄ and n have the same significance as above.

Practically, the compound of the formula II is reacted with an equimolar or excessive molar amount of the compound of the formula III in an organic solvent which does not participate in the reaction in the presence of, as the case may be, an acid catalyst. In this case, it is preferred to perform the reaction under heating, that is, the reaction is preferably performed at a temperature near the boiling point of the solvent used or is performed at a temperature above the boiling point of the solvent in a sealed tube. The reaction is usually performed under refluxing. As an organic solvent which does not participate in the reaction, there are, for example, methanol, ethanol, ether, 2-ethoxyethanol, diglyme, dimethylformamide, xylene, ethylene glycol, and dichlorobenzene. As the acid catalyst used in the reaction, there are, for example, p-toluenesulfonic acid and sulfuric acid. In addition, the compound of the formula II wherein A is a carboxy group may be supplied in the reaction system as the acid anhydride thereof and further the compound of the formula III may be supplied as the addition salt of an acid such as hydrochloric acid, hydrobromic acid, etc. When the acid addition salt of the compound of the formula III is used, the reaction is usually performed in the presence of a base such as sodium acetate, sodium methoxide, sodium ethoxide, etc.

In this case, when the reaction is performed in the absence of an acid catalyst using the compound of the formula III wherein n is 1, the compound shown by the formula IV

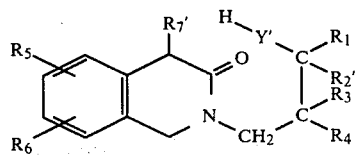

wherein Y', $R_1$, $R_2'$, $R_3$, $R_4$, $R_5$, $R_6$ and $R_7'$ have the same significance as above can be obtained in the case of using the compound of the formula II wherein A is a carboxy group and by heating the compound of the formula IV in the presence of an acid catalyst, the compound of the aforesaid formula Ia wherein n is 1 can be obtained.

In addition, the intermediate compound of the formula IV wherein Y' is a sulfur atom can also be obtained by reacting the compound of the formula II wherein A is a carboxy group with the compound shown by the formula V

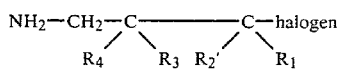

wherein $R_1$, $R_2'$, $R_3$ and $R_4$ have the same significance as above and then reacting the product with hydrogen sulfide, sodium hydrosulfide, etc.

(B). The compound of this invention shown by the formula I wherein Y is a sulfur atom and $R_2$ is a hydrogen atom or a lower alkyl group, that is the compound of this invention shown by the formula Ib

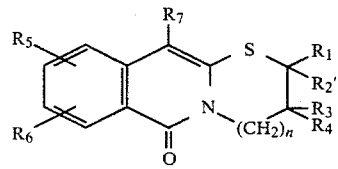

wherein $R_1$, $R_2'$, $R_3$, $R_4$, $R_5$, $R_6$, $R_7$ and n have the same significance as above can be prepared by reacting the compound shown by the formula VI

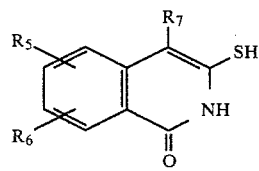

wherein $R_5$, $R_6$ and $R_7$ have the same significance as above with the compound shown by the formula VII

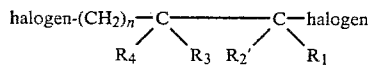

wherein $R_1$, $R_2'$, $R_3$, $R_4$ and n have the same significance as above. Practically, the compound of the formula VI is reacted with an equimolar or excessive molar amount of the compound of the formula VII in an organic solvent which does not participate the in reaction. In this case, it is preferred to perform the reaction in the presence of a base such as an alkali metal alkoxide, e.g., sodium methoxide, sodium ethoxide, etc. It is also preferred to perform the reaction under heating, that is the reaction is preferably carried out at a temperature near the boiling point of the solvent used or is carried out at a temperature above the boiling point of the solvent in a sealed tube. Also, examples of the organic solvents which do not participate in the reaction are methanol, ethanol, ether, 2-ethoxyethanol, diglyme, xylene, ethylene glycol, dichlorobenzene, etc. In addition, the compound of the formula VI may be supplied to the reaction system as the compound shown by the formula VIa

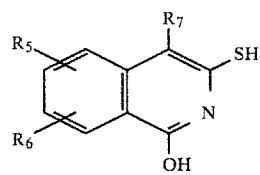

or the compound shown by formula VIb

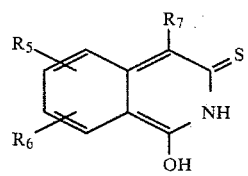

wherein $R_5$, $R_6$ and $R_7$ have the same significance as above.

(C). The compound of this invention shown by the formula I wherein Y is the group shown by

can be prepared from the compound of the formula I wherein Y is a sulfur atom. That is, the compound of this invention shown by the formula Ic

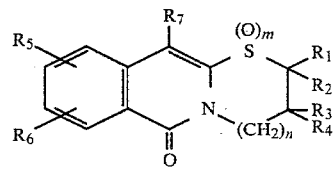

wherein $R_1$, $R_2$, $R_3$, $R_4$, $R_5$, $R_6$, $R_7$, m, and n have the same significance as above can be prepared by oxidizing the compound shown by the formula VIII

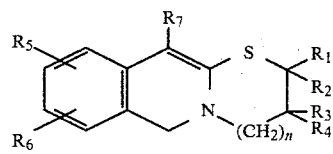

wherein $R_1$, $R_2$, $R_3$, $R_4$, $R_5$, $R_6$, $R_7$ and n have the same significance as above.

Practically, the compound of the formula VIII is dissolved in an organic acid such as acetic acid and is reacted with an oxidizing agent under cooling or at room temperature, or under heating, Conventional oxidizing agents can be employed in the reaction. It is preferred to use 10–40% aqueous hydrogen peroxide solution as the oxidizing agent. In this case, by properly selecting the reaction conditions such as the reaction time, the reaction temperature, the amount of the oxidizing agent, etc., the desired monoxide compound (m=1) or as the desired dioxide compound (m=2) can be obtained.

(D). The compound of this invention shown by the formula I wherein $R_2$ and $R_3$ for together a double bond can be prepared from the compound of the formula I wherein one of $R_2$ and $R_3$ is a hydroxyl group or a lower alkanoyloxy group and the other is a hydrogen atom. That is, the compound of this invention shown by the formula Id

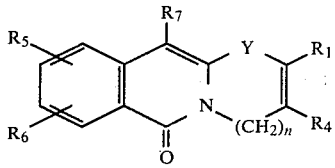

wherein Y, $R_1$, $R_4$, $R_5$, $R_6$, $R_7$ and n have the same significance as above can be prepared by treating the compound shown by the formula IX with an acid

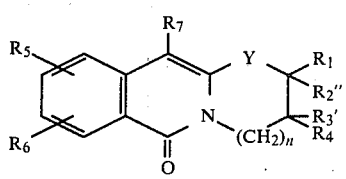

wherein one of $R_2''$ and $R_3'$ is a hydroxyl group or a lower alkanoyloxy group and the other is a hydrogen atom, and Y, $R_1$, $R_4$, $R_5$, $R_6$, $R_7$ and n have the same significance as above.

Practically, the acid treatment is usually performed at room temperature using an acid such as concentrated sulfuric acid, phosphoric acid, etc. In this case, a solvent such as ethanol, etc., may be used. Furthermore, the reaction may be also carried out by heating the compound in an organic solvent using p-toluenesulfonic acid, etc.

(E). The compound of this invention shown by the formula I wherein Y is a sulfur atom and $R_2$ is a lower alkanoyloxy group can be prepared from the compound of the formula I wherein Y is the group shown by $$-\overset{(O)_m}{S}-$$

(wherein m is 1) and $R_2$ is a hydrogen atom. That is, the compound of this invention shown by formula Ie

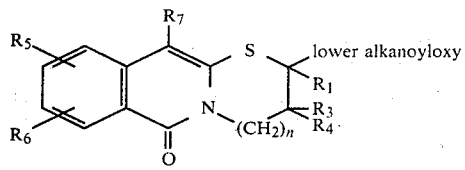

wherein $R_1$, $R_3$, $R_4$, $R_5$, $R_6$ and n have the same significance as above can be prepared by reacting the compound shown by the formula X

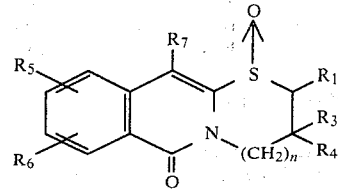

wherein $R_1$, $R_3$, $R_4$, $R_5$, $R_6$ and n have the same significance as above with an acylating agent such as acetic anhydride, etc. In this case, when $R_3$ is a hydrogen atom in the compound of the formula Ie thus obtained, the compound of Id wherein Y is a sulfur atom can be obtained by treating the compound with an acid according to the method (D) without isolating the compound from the reaction mixture.

(F). The compound of the formula I wherein $R_2$ and/or $R_3$ is a hydroxyl group can be prepared by hydrolyzing the compound of the formula I wherein $R_2$ and/or $R_3$ is a lower alkanoyloxy group under an alkaline condition according to a conventional manner.

(G). The compound of this invention shown by the formula I wherein $R_2$ and/or $R_3$ is a lower alkanoyloxy group can be prepared by acylating the compound of the formula I wherein $R_2$ and/or $R_3$ is a hydroxyl group with a corresponding acylating agent such as acetic anhydride, etc., according to a conventional manner.

(H). The compound of this invention shown by the formula I wherein $R_5$ and/or $R_6$ is an amino group can be prepared by catalytic reducing the compound of the formula I wherein $R_5$ and/or $R_6$ is a nitro group according to a conventional manner.

(I). The compound of this invention shown by the formula I wherein $R_5$ and/or $R_6$ is a nitro group can be prepared by nitrating the compound of the formula I wherein at least one of $R_5$ and $R_6$ is a hydrogen atom with nitric acid according to a conventional manner.

(J). The compound of this invention shown by the formula I wherein $R_7$ is a halogen atom can be prepared by halogenating the compound of the formula I wherein $R_7$ is a hydrogen atom with a halogen such as chlorine, bromine, etc., according to a conventional manner.

(K). The compound of this invention shown by the formula I wherein $R_7$ is a lower alkanoyl group can be prepared by acylating the compound of the formula I wherein $R_7$ is a hydrogen atom with a corresponding acyl halide such as acetyl chloride, etc., according to a conventional manner. In addition, the compound of the formula I wherein $R_7$ is a formyl group can also be prepared by reacting the compound of the formula I wherein $R_7$ is a hydrogen atom with a complex of dimethylformamide and phosphorus oxychloride (Vilsmeier reagent) followed by hydrolysis.

(L). The compound of this invention shown by the formula I wherein $R_7$ is a hydroxymethyl group can be prepared by reducing the compound of the formula I wherein $R_7$ is a formyl group according to a conventional manner.

(M). The compound of this invention shown by the formula I wherein $R_7$ is a di-lower alkylaminomethyl group, a pyrrolidinomethyl group, a piperidinomethyl group, a morpholinomethyl group, or a 4-lower alkylpiperazinomethyl group can be prepared from the compound of formula I wherein $R_7$ is a hydrogen atom by a Mannich reaction, that is, by reacting the compound with formaldehyde and a corresponding amine (di-lower alkylamine, etc.,) according to a conventional manner.

(N). The compound of this invention shown by the formula I wherein $R_7$ is a di-lower alkylaminoalkyl group, a pyrrolidino lower alkyl group, a piperidino lower alkyl group, a morpholino lower alkyl group, or a 4-lower alkylpiperazino lower alkyl group can be prepared by halogenating the compound of the formula I wherein $R_7$ is a hydroxy lower alkyl group to form the compound of the formula I wherein $R_7$ is a halogeno lower alkyl group and then reacting the product with a corresponding amine (di-lower alkylamine, etc.) according to a conventional manner.

(O). The compound of this invention shown by the formula I wherein Y is the group shown by

(wherein m is 2) and at least one of $R_1$ and $R_2$ is a lower alkyl group or a lower alkenyl group can be prepared by reacting the compound of the formula I wherein Y is the group shown by

(wherein m is 2) and $R_1$ and $R_2$ are a hydrogen atom and a corresponding lower alkylhalide or a lower alkenylhalide in the presence of a strong base such as sodium amide, potassium amide, etc., according to a conventional manner.

The compounds of this invention shown by the formula I thus prepared can be isolated and purified by an ordinary chemical treatment such as concentration, recrystallization, column chromatography, etc.

Then, the results of the following experiments show the excellent therapeutical activities of the compounds of this invention:

(a) carrageenin-induced edema

Male Wister rats (weighting 130-170 g.), one group being 6 rats, fasted overnight were used. According to Winter's method [Proc. Soc. Exp. Biol. Med., 111,544(1962)], 0.1 ml. of 1% carrageenin [Iwai Kagaku Yakuhin K. K. Seakem] suspension in 0.9% saline was injected into the planter tissue of the left hind paw. After 3 hours, each rat was sacrificed by chloroform and the hind paw was cut and weighed immediately. By using the value obtained by subtracting the weight of the untreated hind paw from the weight of the hind paw having injected thereto the carrageenin as the weight of edema, the inhibitory ratio of the sample administered rat groups to control groups was calculated. The sample was orally administered before one hour of the injection of carrageenin. The results obtained are shown in Table 1.

(b) Whittle's method (British J. Pharmacol.; 22, 246–253 (1964))

Male ICR-Mice (weighting 25–35 g.), one group being 12 mice, fasted overnight were used in this test. The sample was orally administered, and 20 minutes after, 5 ml./Kg. of 0.4% Evance blue was injected intravenously and further 10 minutes after, 10 ml./Kg. of 0.6% acetic acid was injected intraperitoneally. The number of writhings after 20 minutes since the administration of acetic acid was recorded and further 10 minutes after since then, the mice were killed by dislocation of the neck, the dye leaked in the abdominal cavity was washed out with 5 ml. of 0.9% saline to make the total amount 10 ml., and thereafter furs, blood corpuscles, etc., intermingled were removed by centrifugal separation at 3,000 r.p.m. for 5 minutes. Furthermore, for preventing turbidity caused by protein, 0.1 ml. of an aqueous 0.1 normal sodium hydroxide was added and then the absorbance at 590 nm was measured. The inhibition ratio of the sample administered rat groups to control groups was calculated. The results are shown in Table 2.

(c) Antipyretic effect

Male Wister rats (weighting 130-150 g.), one group being 5 rats, were used. Hyperthermia was caused by subcutaneous injection of 2 ml./rat of 20% Brewer's yeast suspension. 18 hours later, the rats showing a rise in temperature exceeding 1° C. were selected and allocated into groups each consisting of 5 rats. The sample was orally administered and then the body temperature was measured with the passage of time for 6 hours since then. In addition, the body temperature was measured by measuring the temperature in the rectum by means of a thermister thermometer. The results are shown in Table 3.

(d) Acute toxicity

Male Wister rats (weighting 130-170 g.), one group being 5 rats, fasted overnight were used in this test. After orally administering 500 mg./Kg. of a sample, they were observed for 7 days to determine whether they were living or dead. The results are shown in Table 4.

In addition, the test samples used in the aforesaid tests (a), (b), (c) and (d) were prepared by suspending the test compounds, in the cases of using the compounds of Test Nos. 1–12 and phenylbutazone, in an aqueous 0.5% methyl cellulose solution, dissolving the test compounds, in the cases of using aminopyrine, in distilled water.

TABLE 1

(Carrageenin-induced edema)

| Test No. | Sample | Dose (mg/kg) | Inhibition (%) |
|---|---|---|---|
| 1 | 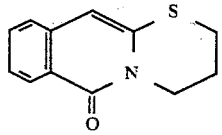 | 25<br>50 | 54.8<br>69.8 |
| 2 | 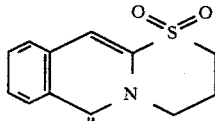 | 25<br>50 | 41.7<br>71.2 |
| 3 | 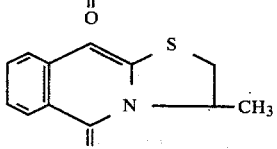 | 25<br>50 | 47.0<br>74.0 |
| 4 | 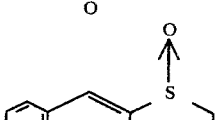 | 25<br>50 | 41.2<br>65.1 |

TABLE 1-continued
(Carrageenin-induced edema)

| Test No. | Sample | Dose (mg/kg) | Inhibition (%) |
|---|---|---|---|
| 5 | [isoquinolinone with S=O side chain] | 25 / 50 | 55.3 / 67.2 |
| 6 | [Cl-substituted isoquinolinone with S side chain] | 25 | 57.1 |
| 7 | [Cl-substituted isoquinolinone with S=O side chain] | 25 | 57.0 |
| 8 | [Cl-substituted isoquinolinone with S=O shorter chain] | 25 | 57.5 |
| 9 | [Cl-substituted isoquinolinone with S-CH3] | 25 | 53.4 |
| 10 | [Cl-substituted isoquinolinone with S=O, CH3] | 25 | 58.0 |
| 11 | [CHO-substituted isoquinolinone with S side chain] | 25 | 45.9 |
| 12 | [CH3, S=O isoquinolinone] | 50 | 71.3 |
| | Phenylbutazone | 25 / 50 | 29.4 / 44.5 |

TABLE 2
(Whittle's method)

| | Inhibition (%) | | | |
|---|---|---|---|---|
| | Writhings | | Permeability | |
| Sample | 25mg/kg P.O. | 50mg/kg P.O. | 25mg/kg P.O. | 50mg/kg P.O. |
| Compound of | | | | |
| Test No. 1 | 24.8 | 57.8 | 26.2 | 21.3 |
| Test No. 2 | 22.6 | 14.4 | 4.7 | 20.1 |
| Test No. 3 | — | 67.5 | — | 37.0 |
| Test No. 4 | 29.1 | 39.7 | 22.1 | 41.1 |
| Test No. 5 | 12.9 | 58.6 | 22.6 | 36.0 |
| Test No. 6 | — | 28.8 | — | 37.1 |
| Test No. 7 | — | 69.5 | — | 38.6 |
| Test No. 8 | — | 74.3 | — | 23.5 |
| Test No. 9 | — | 82.9 | — | 34.1 |
| Test No. 10 | — | 91.6 | — | 32.4 |
| Aminopyrine | 29.6 | 58.1 | 28.5 | 41.7 |

TABLE 3
(Antipyretic effect)

| Sample | Dose (P.O.) | Rectal temperature (mean ± SE) | | | | |
|---|---|---|---|---|---|---|
| | | before | 1 hour | 2 hours | 4 hours | 6 hours |
| Compound of | | | | | | |
| Test No. 1 | 50mg/kg | 39.26 ± 0.19 | *38.72 ± 0.13 | *38.20 ± 0.15 | *37.39 ± 0.23 | *37.44 ± 0.32 |
| Test No. 2 | 50mg/kg | 38.94 ± 0.14 | 39.04 ± 0.23 | 38.41 ± 0.21 | *37.32 ± 0.31 | *37.55 ± 0.33 |
| Aminopyrine | 50mg/kg | 39.24 ± 0.14 | *37.92 ± 0.09 | *37.49 ± 0.10 | *37.39 ± 0.07 | *37.76 ± 0.19 |
| 0.9% saline | 10ml/kg | 39.06 ± 0.16 | 39.56 ± 0.32 | 39.28 ± 0.23 | 39.11 ± 0.16 | 39.31 ± 0.19 |

[*significantly different from the temperature before administration ($p < 0.05$)]

TABLE 4
(Acute toxicity)

| Sample | Number of death Mouse |
|---|---|
| Compound of Test No. 1 | 1/5 |
| Compound of Test No. 2 | 0/5 |
| Compound of Test No. 3 | 3/5 |
| Compound of Test No. 4 | 3/5 |
| Compound of Test No. 5 | 3/5 |

From the test results by the aforesaid carrageenin-induced edema and Wittle's method, it is clear that the compounds I of this invention have excellent anti-inflammatory activity and excellent analgesic activity. Furthermore, from the results by the antipyretic effect, it is also clear that the compounds of this invention shown by formula I have excellent antipyretic activity.

The clinical doses of the compounds I of this invention are usually 100–1,000 mg., preferably 150–600 mg. per day for an adult and the medicament is administered 2–3 times per day. The doses are properly controlled according to the condition and age of the patient.

The compounds of this invention are administered as various forms such as agents for oral administration, injections, suppositories for rectal administration, medicines for topical application, etc.

The medicaments of this invention are used as compositions prepared by blending with conventional pharmaceutical carriers or excipients by ordinary method. The tablets, capsules, granules, powders, etc., of the compounds of this invention for oral administration may contain an pharmaceutical excipient generally used in the field of art, such as calcium carbonate, calcium phosphate, starch, sucrose, lactose, talc, magnesium stearate, gelatin, polyvinyl pyrrolidone, gum arabic, sorbitol, microcrystalline cellulose, polyethylene glycol, silica, sodium laurylsulfate, etc. Moreover, the tablets may be coated by a manner well known in the art.

Furthermore, the liquid formulations for oral administration may be an aqueous or oily suspension, a syrup, an elixir, etc., and are prepared by a conventional method.

Suppositories for rectal use are used and they may contain a formulation carrier well known in the art, such as polyethylene glycol, lanolin, cacao butter, Witepsol ® (made by Dynamite Nobel Co.), etc.

Then, examples of the formulations of the medicaments of this invention are shown below:

Formulation example 1

Tablets containing the compounds of this invention shown by formula I, the weight of one tablet being 300 mg.
Compound of formula I: 1,000 g.
Lactose: 1,200 g.
Starch: 770 g.
Magnesium stearate: 30 g.

A 10% starch paste was prepared using a part of starch described above and after adding the starch paste as a binder to a mixture of the compounds of formula I, lactose and remaining starch, the resultant mixture was granulated by a conventional manner. Then, magnesium stearate was added to the granules and the mixture was molded into 10,000 tablets each having a diameter of 9.5 mm. and weight of 300 mg. The active component was 100 mg./tablet.

Formulation example 2

Capsules containing the compounds I of this invention, the weight of one capsule being 300 mg.
Compound of formula I: 1,000 g.
Lactose: 1,200 g.
Starch: 770 g.
Magnesium stearate: 30 g.

After mixing well 1,000 g. of the compound of formula I, 1,200 g. of lactose, 770 g. of starch, and 30 g. of magnesium stearate, the mixture was filled in 10,000 capsules. The weight of each capsule filled with the mixture was 300 mg. The active component was 100 mg./capsule.

EXAMPLE 1

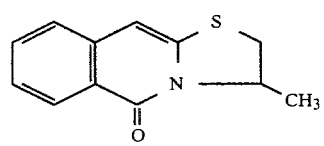

In 10 ml. of acetic acid were dissolved 3.6 g. of 2-carboxymethylbenzoic acid and 1.3 g. of 2-aminopropanethiol.hydrochloride and after further adding 3.3 g. of sodium acetate to the solution, the resultant mixture was refluxed for 3 hours. After the reaction was over, the reaction mixture was cooled, poured into 50 ml. of ice water, and extracted three times each time with 20 ml. of ethyl acetate. The extracts were combined with each other, washed with a 10% aqueous sodium carbonate solution and water, and after drying over anhydrous magnesium sulfate, the solvent was distilled off. The crystals formed were recovered and recrystallized from ethanol to provide 1.1 g. of 3-methyl-5-oxo-2,3-dihydro-5H-thiazolo[3,2-b]isoquinoline.

Melting point 83°–84° C.

Elemental analysis for $C_{12}H_{11}NSO$:

|  | C | H | N | S |
|---|---|---|---|---|
| Found: | 66.20% | 4.84% | 6.51% | 14.27% |
| Calculated: | 66.33% | 5.10% | 6.45% | 14.75% |

EXAMPLE 2

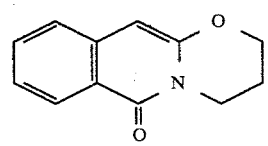

In 10 ml. of o-dichlorobenzene were dissolved 3.6 g. of 2-carboxymethylbenzoic acid and 1.5 g. of 3-aminopropanol and after refluxing the solution for 4 hours, 100 mg. of p-toluenesulfonic acid was added to the solution followed by further refluxing for 3 hours. After the reaction was over, the reaction mixture was cooled, applied to a silica gel column chromatography using 30 g. of silica gel, purified by a mixture of ethanol and chloroform (1:99 by volume ratio), and the crude crystals obtained were recrystallized from ethanol to provide 0.7 g. of 6-oxo-2,3-dihydro-2H,6H-1,3-oxazino[3,2-b]isoquinoline.

Melting point 100°–101° C.

Elemental analysis for $C_{12}H_{11}NO_2$:

|  | C | H | N |
|---|---|---|---|
| Found: | 71.61% | 5.53% | 6.85% |
| Calculated: | 71.63% | 5.51% | 6.96% |

EXAMPLE 3

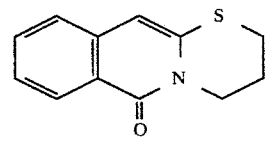

In 20 ml. of o-dichlorobenzene were dissolved 7.2 g. of 2-carboxymethylbenzoic acid and 5.2 g. of 3-aminopropanethiol hydrochloride and after adding 6.6 g. of sodium acetate to the solution, the resultant mixture was refluxed for 3 hours. The precipitates thus formed were filtered off and 3 g. of p-toluenesulfonic acid was added to the filtrate followed by refluxing for one hour. After the reaction was over, the reaction mixture was cooled, applied to a silica gel column chromatography using 80 g. of silica gel, and purified by a mixture of ethanol and chloroform (1:99 by volume ratio). The fractions containing the desired product were collected, the solvent was distilled off, and the crude crystals obtained were recrystallized from ethanol to provide 3.0 g. of 6-oxo-3,4-dihydro-2H,6H-1,3-thiazino[3,2-b]isoquinoline.

Melting point 85°–86° C.
Elemental analysis for $C_{12}H_{11}NSO$:

|  | C | H | N | S |
|---|---|---|---|---|
| Found: | 66.16% | 4.91% | 6.22% | 14.58% |
| Calculated: | 66.33% | 5.10% | 6.45% | 14.75% |

EXAMPLE 4

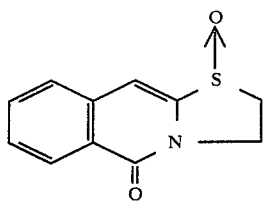

In 10 ml. of acetic acid was dissolved 1.0 g. of 5-oxo-2,3-dihydro-5H-thiazolo[3,2-b]isoquinoline and after adding 0.68 g. of a 30% aqueous hydrogen peroxide solution to the solution under ice-cooling, the resultant mixture was allowed to stand overnight at room temperature. The reaction mixture obtained was concentrated under reduced pressure and the crude crystals formed were recovered and recrystallized from 20 ml. of ethanol to provide 650 mg. of 5-oxo-2,3-dihydro-5H-thiazolo[3,2-b]isoquinoline-1-oxide.

Melting point 160°–162° C.
Elemental analysis for $C_{11}H_9NSO_2$:

|  | C | H | N | S |
|---|---|---|---|---|
| Found: | 60.28% | 4.07% | 6.33% | 14.56% |
| Calculated: | 60.26% | 4.14% | 6.39% | 14.62% |

EXAMPLE 5

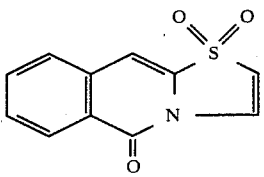

In one ml. of acetic acid was dissolved 50 mg. of 5-oxo-5H-thiazolo[3,2-b]isoquinoline and after adding 0.05 ml. of a 30% aqueous hydrogen peroxide solution to the solution, the resultant mixture was heated to 80° C. for 8 hours. After the reaction was over, the reaction mixture was cooled and the crystals precipitated were recovered to provide 35 mg. of 5-oxo-5H-thiazolo[3,2-b]isoquinoline-1,1-dioxide.

Melting point 256°–260° C.
Elemental analysis for $C_{11}H_7NSO_3$

|  | C | H | N | S |
|---|---|---|---|---|
| Found: | 56.43% | 3.25% | 5.82% | 14.01% |
| Calculated: | 56.64% | 3.03% | 6.01% | 13.75% |

EXAMPLE 6

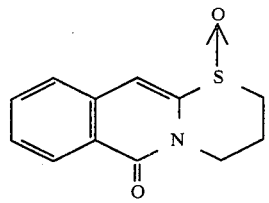

In 10 ml. of acetic acid was dissolved 1.65 g. of 6-oxo-3,4-dihydro-2H,6H-1,3-thiazino[3,2-b]isoquinoline and after adding 0.84 g. of a 30% aqueous hydrogen peroxide solution to the solution, the resultant mixture was treated as in Example 4 to provide 900 mg. of 6-oxo-3,4-dihydro-2H,6H-1,3-thiazino[3,2-b]isoquinoline-1-oxide.

Melting point 132°–133° C.
Elemental analysis for $C_{12}H_{11}SNO_2$:

|  | C | H | N | S |
|---|---|---|---|---|
| Found: | 61.85% | 4.36% | 5.67% | 13.47% |
| Calculated: | 61.78% | 4.75% | 6.00% | 13.74% |

EXAMPLE 7

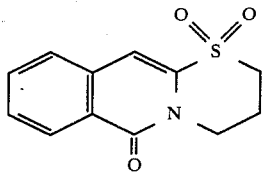

In 10 ml. of acetic acid was dissolved 0.8 g. of 6-oxo-3,4-dihydro-2H,6H-1,3-thiazino[3,2-b]isoquinoline and after adding 0.84 g. of a 30% aqueous hydrogen peroxide solution, the resultant mixture was refluxed for 2 hours. After the reaction was over, the reaction mixture was concentrated under reduced pressure and the crude crystals obtained were recrystallized from 100 ml. of ethanol to provide 550 mg. of 6-oxo-3,4-dihydro-2H,6H-1,3-thiazino[3,2-b]isoquinoline-1,1-dioxide.

Melting point 206°–208° C.
Elemental analysis for $C_{12}H_{11}SNO_3$:

|  | C | H | N | S |
|---|---|---|---|---|
| Found: | 57.69% | 4.32% | 5.58% | 12.72% |
| Calculated: | 57.82% | 4.45% | 5.62% | 12.86% |

EXAMPLE 8

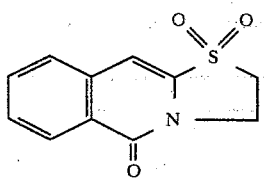

By following the same procedure as in Example 7 using 1.0 g. of 5-oxo-2,3-dihydro-5H-thiazolo[3,2-b]isoquinoline and 1.4 g. of a 30% aqueous hydrogen peroxide solution, 550 mg. of 5-oxo-2,3-dihydro-5H-thiazolo[3,2-b]isoquinoline-1,1-dioxide was obtained.

Melting point 208°–211° C.
Elemental analysis for $C_{11}H_9NSO_3$:

|  | C | H | N | S |
|---|---|---|---|---|
| Found: | 56.04% | 3.66% | 5.85% | 13.11% |
| Calculated: | 56.16% | 3.87% | 5.95% | 13.63% |

EXAMPLE 9

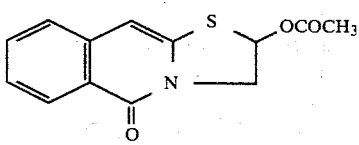

In 20 ml. of acetic anhydride were dissolved 2.0 g. of 5-oxo-2,3-dihydro-5H-thiazolo[3,2-b]isoquinoline-1-oxide and 0.2 g. of sodium acetate and the solution was refluxed for 12 hours. After cooling, the reaction mixture obtained was poured into 200 ml. of water and the crude crystals thus precipitated were recovered by filtration and then recrystallized from 20 ml. of ethanol to provide 1.6 g. of 2-acetoxy-5-oxo-2,3-dihydro-5H-thiazolo[3,2-b]isoquinoline.

Melting point 141°–143° C.
Elemental analysis for $C_{13}H_{11}SNO_3$:

|  | C | H | N | S |
|---|---|---|---|---|
| Found: | 59.80% | 4.09% | 5.22% | 12.05% |
| Calculated: | 59.76% | 4.24% | 5.36% | 12.27% |

EXAMPLE 10

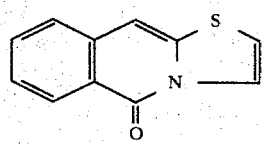

In 5 ml. of concentrated sulfuric acid was dissolved 1.1 g. of 2-acetoxy-5-oxo-2,3-dihydro-5H-thiazolo[3,2-b]isoquinoline and the solution was allowed to stand for one hour at room temperature. The reaction mixture obtained was added to 50 ml. of ice water and extracted three times each time with 15 ml. of ethyl acetate. The extracts were combined with each other and after washing with water, the extract was dried over anhydrous magnesium sulfate. Then, the solvent was distilled off under reduced pressure and the crude crystals obtained were recrystallized from ethanol to provide 500 mg. of 5-oxo-5H-thiazolo[3,2-b]isoquinoline.

Melting point 135°–136° C.
Elemental analysis for $C_{11}H_7NSO$:

|  | C | H | N | S |
|---|---|---|---|---|
| Found: | 65.39% | 3.40% | 6.69% | 15.37% |
| Calculated: | 65.65% | 3.51% | 6.96% | 15.93% |

EXAMPLE 11

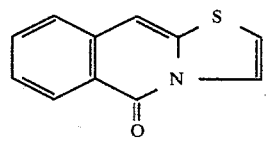

By following the same procedure as in Example 10 using 55 mg. of 2-hydroxy-5-oxo-2,3-dihydro-5H-thiazolo[3,2-b]isoquinoline, 40 mg. of 5-oxo-5H-thiazolo[3,2-b]isoquinoline was obtained.

Melting point 135°–136° C.

EXAMPLE 12

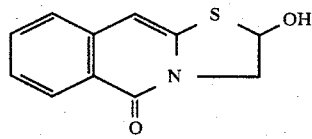

In 5 ml. of methanol was dissolved 250 mg. of 2-acetoxy-5-oxo-2,3-dihydro-5H-thiazolo[3,2-b]isoquinoline and after adding 5 ml. of a 1 normal aqueous sodium hydroxide solution to the solution, the resultant mixture was allowed to stand overnight at room temperature. The reaction mixture obtained was concentrated to about a half volume thereof and extracted with 5 ml. of ethyl acetate. The extracts were combined with each other and the solvent was distilled off under reduced pressure. The crystals thus formed were recovered by filtration and recrystallized from 10 ml. of ethanol to provide 165 mg. of 2-hydroxy-5-oxo-2,3-dihydro-5H-thiazolo[3,2-b]isoquinoline.

Melting point 215°–217° C.
Elemental analysis for $C_{11}H_9NSO_2$:

|  | C | H | N | S |
|---|---|---|---|---|
| Found: | 60.01% | 3.89% | 6.36% | 14.23% |
| Calculated: | 60.26% | 4.14% | 6.39% | 14.62% |

EXAMPLE 13

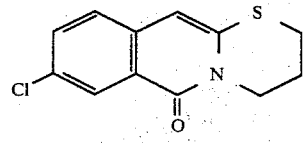

In 10 ml. of o-dichlorobenzene were dissolved 2.5 g. of 2-carboxymethyl-5-chlorobenzoic acid and 2.2 g. of 3-aminopropanethiol hydrobromide and after further adding 1.0 g. of sodium acetate to the solution, the resulta mixture was heated to 150°–160° C. for 2 hours with stirring. Then, 2.0 g. of p-toluenesulfonic acid was added to the reaction mixture at 140°–150° C. followed by stirring for 20 minutes, the reaction mixture was cooled to room temperature. The precipitates formed were filtered off and the filtrate was distilled under reduced pressure. To the residue formed was added isopropanol and the crystals formed were recovered by filtration and recrystallized from isopropanol to provide 1.9 g. of 8-chloro-6-oxo-3,4-dihydro-2H,6H-1,3-thiazino[3,2-b]isoquinoline.

Melting point 117°–118° C.

Elemental analysis for $C_{12}H_{10}NOSCl$:

|  | C | H | N | S | Cl |
|---|---|---|---|---|---|
| Found: | 57.01% | 3.98% | 5.32% | 12.84% | 13.94% |
| Calculated: | 57.26% | 4.00% | 5.56% | 12.74% | 14.08% |

EXAMPLE 14

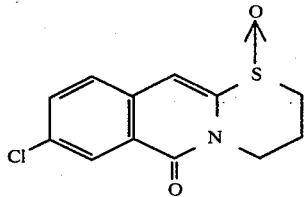

In 3 ml. of glacial acetic acid was dissolved 500 mg. of 8-chloro-6-oxo-3,4-dihydro-2H,6H-1,3-thiazino[3,2-b]isoquinoline and after adding 0.23 ml. of a 30% aqueous hydrogen peroxide solution to the solution under ice-cooling, the resultant mixture was allowed to stand overnight at room temperature. The reaction mixture obtained was poured in ice water and the crystals precipitated were recovered by filtration and recrystallized from ethanol to provide 380 mg. of 8-chloro-6-oxo-3,4-dihydro-2H,6H-1,3-thiazino[3,2-b]isoquinoline-1-oxide.

Melting point 147°–148° C.

Elemental analysis for $C_{12}H_{10}NO_2SCl$:

|  | C | H | N | S | Cl |
|---|---|---|---|---|---|
| Found: | 53.61% | 3.70% | 4.99% | 11.96% | 13.27% |
| Calculated: | 53.83% | 3.76% | 5.23% | 11.98% | 13.24% |

EXAMPLE 15

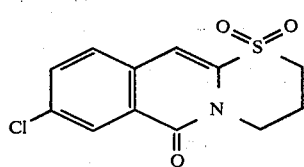

In 3 ml. of glacial acetic acid was dissolved 500 mg. of 8-chloro-6-oxo-3,4-dihydro-2H,6H-1,3-thiazino[3,2-b]isoquinoline and after adding 0.5 ml. of a 30% aqueous hydrogen peroxide solution to the solution, the resultant mixture was heated to 70°–80° C. for 3 hours. After the reaction was over, the reaction mixture was cooled and the crystals precipitated were recovered by filtration and recrystallized from glacial acetic acid to provide 400 mg. of 8-chloro-6-oxo-3,4-dihydro-2H,6H-1,3-thiazino[3,2-b]isoquinoline-1,1-dioxide.

Melting point 234°–235° C.

Elemental analysis for $C_{12}H_{10}NO_3SCl$:

|  | C | H | N | S | Cl |
|---|---|---|---|---|---|
| Found: | 50.47% | 3.45% | 4.94% | 11.56% | 12.75% |
| Calculated: | 50.80% | 3.55% | 4.94% | 11.30% | 12.50% |

EXAMPLE 16

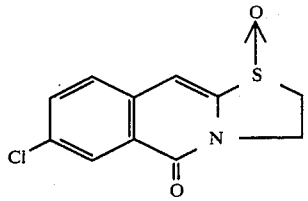

In 5 ml. of glacial acetic acid was dissolved 475 mg. of 7-chloro-5-oxo-2,3-dihydro-5H-thiazolo[3,2-b]isoquinoline and after adding 0.19 ml. of a 35% aqueous hydrogen peroxide solution to the solution under ice-cooling, the resultant mixture was allowed to stand overnight at room temperature. The reaction mixture obtained was poured into ice water and the crystals precipitated were recovered by filtration and recrystallized from ethanol to provide 300 mg. of 7-chloro-5-oxo-2,3-dihydro-5H-thiazolo[3,2-b]isoquinoline-1-oxide.

Melting point 216°–217° C.

Elemental analysis for $C_{11}H_8NO_2SCl$:

|  | C | H | N | S | Cl |
|---|---|---|---|---|---|
| Found: | 51.82% | 3.04% | 5.43% | 12.39% | 14.17% |
| Calculated: | 52.08% | 3.18% | 5.52% | 12.64% | 13.97% |

EXAMPLE 17

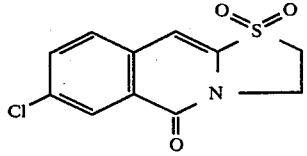

In 5 ml. of glacial acetic acid was dissolved 650 mg. of 7-chloro-5-oxo-2,3-dihydro-5H-thiazolo[3,2-b]isoquinoline and after adding 0.8 ml. of a 35% aqueous hydrogen peroxide solution to the solution, the resultant mixture was refluxed for 2 hours. After the reaction was over, the reaction mixture was cooled and the crystals precipitated were recovered by filtration and recrystallized from glacial acetic acid to provide 500 mg. of 7-chloro-5-oxo-2,3-dihydro-5H-thiazolo-[3,2-b]isoquinoline-1,1-dioxide.

Melting point 255°–256° C.

Elemental analysis for $C_{11}H_8NO_3SCl$:

|  | C | H | N | S | Cl |
|---|---|---|---|---|---|
| Found: | 48.73% | 2.94% | 5.14% | 11.93% | 12.99% |

| | C | H | N | S | Cl |
|---|---|---|---|---|---|
| Calculated: | 48.99% | 2.99% | 5.19% | 11.89% | 13.14% |

EXAMPLE 18

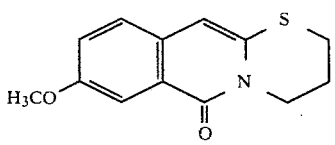

In 10 ml. of o-dichlorobenzene were dissolved 1.6 g. of 2-carboxymethyl-5-methoxybenzoic acid and 1.6 g. of 3-aminopropanethiol hydrobromide and after adding 0.8 g. of sodium acetate to the solution, the resultant mixture was heated to 150°–160° C. for 2 hours with stirring. Then, 1.3 g. of p-toluenesulfonic acid was added to the reaction mixture at 140°–150° C. followed by stirring for 30 minutes, the reaction mixture was cooled to room temperature. The precipitates formed were filtered off and the filtrate was distilled under reduced pressure. The solid residue formed was recrystallized from isopropanol to provide 1.0 g. of 8-methoxy-6-oxo-3,4-dihydro-2H,6H-1,3-thiazino[3,2-b]isoquinoline.

Melting point 125°–126° C.

Elemental analysis for $C_{13}H_{13}NO_2S$:

| | C | H | N | S |
|---|---|---|---|---|
| Found: | 62.95% | 5.25% | 5.49% | 12.70% |
| Calculated: | 63.14% | 5.30% | 5.66% | 12.96% |

EXAMPLE 19

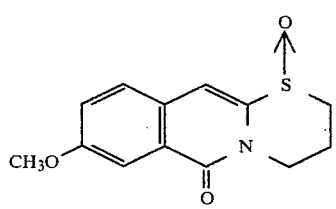

In 5 ml. of glacial acetic acid was dissolved 300 mg. of 8-methoxy-6-oxo-3,4-dihydro-2H,6H-1,3-thiazino[3,2-b]isoquinoline and after adding 0.12 ml. of a 35% aqueous hydrogen peroxide solution to the solution under ice-cooling, the resultant mixture was allowed to stand overnight at room temperature. The reaction mixture obtained was poured into ice water and extracted three times each time with 10 ml. of chloroform. The extracts were combined with each other, washed successively with 1 N hydrochloric acid, a 10% aqueous sodium carbonate solution, and then water, dried over anhydrous sodium sulfate, and the solvent was distilled off under reduced pressure.

The crude crystals obtained were recrystallized from ethanol to provide 220 mg. of 8-methoxy-6-oxo-3,4-dihydro-2H,6H-1,3-thiazino[3,2-b]isoquinoline-1-oxide.

Melting point 188°–189° C.

Elemental analysis for $C_{13}H_{13}NO_3S$:

| | C | H | N | S |
|---|---|---|---|---|
| Found: | 59.01% | 4.99% | 5.11% | 12.12% |
| Calculated: | 59.30% | 4.98% | 5.32% | 12.18% |

EXAMPLE 20

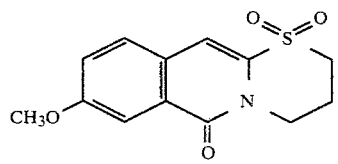

In 5 ml. of glacial acetic acid was dissolved 350 mg. of 8-methoxy-6-oxo-3,4-dihydro-2H,6H-1,3-thiazino[3,2-b]isoquinoline and after adding 0.28 ml. of a 35% aqueous hydrogen peroxide solution to the solution, the resultant mixture was heated to 60°–70° C. for 2 hours. The reaction mixture obtained was cooled and the crystals precipitated were recovered by filtration and recrystallized from glacial acetic acid to provide 240 mg. of 8-methoxy-6-oxo-3,4-dihydro-2H,6H-1,3-thiazino[3,2-b]isoquinoline-1,1-dioxide.

Melting point 215°–216° C.

Elemental analysis for $C_{13}H_{13}NO_4S$:

| | C | H | N | S |
|---|---|---|---|---|
| Found: | 55.52% | 4.66% | 4.92% | 11.30% |
| Calculated: | 55.90% | 4.69% | 5.01% | 11.48% |

EXAMPLE 21

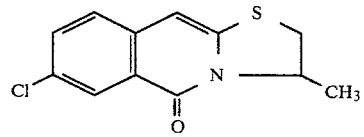

In 10 ml. of glacial acetic acid were dissolved 1.5 g. of 2-carboxymethyl-5-chlorobenzoic acid and 900 mg. of 2-aminopropanethiol hydrochloride and after adding 1.2 g. of sodium acetate to the solution, the resultant mixture was refluxed overnight. After the reaction was over, the reaction mixture was cooled, poured in ice water and extracted three times each time with 20 ml. of ethyl acetate. The extracts were combined with each other, washed with a 10% aqueous sodium carbonate solution and water, and after drying over anhydrous sodium sulfate, the solvent was distilled off under reduced pressure. The crude crystals obtained were recrystallized from isopropanol to provide 800 mg. of 7-chloro-3-methyl-5-oxo-2,3-dihydro-5H-thiazolo[3,2-b]isoquinoline.

Melting point 120°–121° C.

Elemental analysis for $C_{12}H_{10}NOSCl$:

| | C | H | N | S | Cl |
|---|---|---|---|---|---|
| Found: | 57.12% | 3.74% | 5.57% | 12.60% | 14.27% |
| Calculated: | 57.26% | 4.00% | 5.56% | 12.74 | 14.08% |

EXAMPLE 22

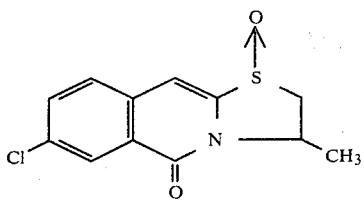

In 5 ml. of glacial acetic acid was dissolved 500 mg. of 7-chloro-3-methyl-5-oxo-2,3-dihydro-5H-thiazolo[3.2-b]isoquinoline and after adding 0.22 ml. of a 30% aqueous hydrogen peroxide solution to the solution under ice-cooling, the resultant mixture was allowed to stand for 48 hours at room temperature. The reaction mixture obtained was poured into ice water and extracted three times each time with 10 ml. of chloroform. The extracts were combined with each other, washed with a 10% aqueous sodium carbonate solution and water, dried over anhydrous sodium sulfate, and the solvent was distilled off under reduced pressure. The crude crystals thus obtained were recrystallized from ethanol to provide 250 mg. of 7-chloro-3-methyl-5-oxo-2,3-dihydro-5H-thiazolo[3,2-b]isoquinoline-1-oxide.

Melting point 171°–172° C.

Elemental analysis for $C_{12}H_{10}NO_2SCl$:

|  | C | H | N | S | Cl |
|---|---|---|---|---|---|
| Found: | 53.85% | 4.01% | 4.87% | 11.65% | 12.93% |
| Calculated: | 53.83% | 3.76% | 5.23% | 11.98% | 13.24% |

EXAMPLE 23

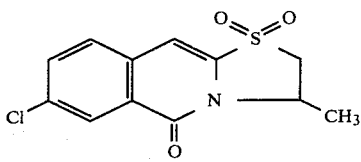

In 5 ml. of glacial acetic acid was dissolved 640 mg. of 7-chloro-3-methyl-5-oxo-2,3-dihydro-5H-thiazolo[3,2-b]isoquinoline and after adding 0.6 ml. of a 30% aqueous hydrogen peroxide solution to the solution, the resultant mixture was refluxed for 2 hours. After the reaction was over, the reaction mixture was cooled and the crystals precipitated were recovered by filtration and recrystallized from glacial acetic acid to provide 290 mg. of 7-chloro-3-methyl-5-oxo-2,3-dihydro-5H-thiazolo[3,2-b]isoquinoline-1,1-dioxide.

Melting point 226°–227° C.

Elemental analysis for $C_{12}H_{10}NO_3SCl$:

|  | C | H | N | S | Cl |
|---|---|---|---|---|---|
| Found: | 50.59% | 3.84% | 4.96% | 11.33% | 12.26% |
| Calculated: | 50.80% | 3.55% | 4.94% | 11.30% | 12.50% |

EXAMPLE 24

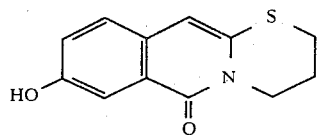

In 10 ml. of o-dichlorobenzene were dissolved 1.0 g. of 2-carboxymethyl-5-hydroxybenzoic acid and 1.1 g. of 3-aminopropanethiol hydrobromide and after adding 520 mg. of sodium acetate to the solution, the resultant mixture was heated to 150°–160° C. with stirring. Then, 800 mg. of p-toluenesulfonic acid was added to the reaction mixture at 120°–130° C. followed by stirring for 30 minutes, the reaction mixture was distilled off under reduced pressure. The residue formed was poured in water and crystals thus precipitated were recovered by filtration and recrystallized from isopropanol to provide 500 mg. of 8-hydroxy-6-oxo-3,4-dihydro-2H,6H-1,3-thiazino[3,2-b]isoquinoline.

Melting point 230°–231° C.

Elemental analysis for $C_{12}H_{11}NO_2S$:

|  | C | H | N | S |
|---|---|---|---|---|
| Found: | 61.64% | 4.61% | 5.87% | 13.85% |
| Calculated: | 61.78% | 4.75% | 6.00% | 13.74% |

EXAMPLE 25

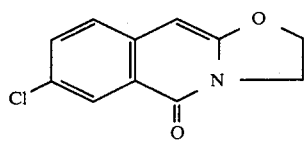

In 5 ml. of o-dichlorobenzene were dissolved 645 mg. of 2-carboxymethyl-5-chlorobenzoic acid and 185 mg. of 2-aminoethanol and after adding 100 mg. of p-toluenesulfonic acid to the solution, the resultant mixture was heated to 150°–160° C. for 3 hours with stirring. The reaction mixture was distilled off under reduced pressure and the residue formed was extracted with 30 ml. of benzene. The extract was successively washed with 1 N hydrochloric acid, a 10% aqueous sodium carbonate solution, and water, dried over anhydrous sodium sulfate, and then the solvent was distilled off under reduced pressure. The residue formed was applied to a silica gel column chromatography, purified using chloroform as an eluting solution, and the crude crystals obtained were further recrystallized from ethanol to provide 170 mg. of 7-chloro-5-oxo-2,3-dihydro-5H-oxazolo[3,2-b]isoquinoline.

Melting point 138°–139° C.

Elemental analysis for $C_{11}H_8NO_2Cl$:

|  | C | H | N | Cl |
|---|---|---|---|---|
| Found: | 59.37% | 3.56% | 6.14% | 16.25% |
| Calculated: | 59.61% | 3.64% | 6.32% | 16.00% |

EXAMPLE 26

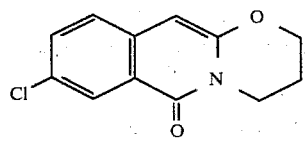

In 5 ml. of o-dichlorobenzene were dissolved 640 mg. of 2-carboxymethyl-5-chlorobenzoic acid and 225 mg. of 3-aminopropanol and after adding 100 mg. of p-toluenesulfonic acid to the solution, the resultant mixture was refluxed for 2 hours with stirring. After the reaction was over, the reaction mixture was distilled under reduced pressure and the residue formed was extracted with 30 ml. of benzene. The extract was successively washed with 1 N hydrochloric acid, a 10% aqueous sodium carbonate solution, and water, dried over anhydrous sodium sulfate, and then the solvent was distilled off under reduced pressure. The residue formed was applied to a silica gel column chromatography, purified using chloroform as an eluting solution, and the crude crystals obtained were further recrystallized from ethanol to provide 190 mg. of 8-chloro-6-oxo-3,4-dihydro-2H,6H-1,3-oxazino[3,2-b]isoquinoline.

Melting point 115°–116° C.

Elemental analysis for $C_{12}H_{10}NO_2Cl$:

|  | C | H | N | Cl |
|---|---|---|---|---|
| Found: | 61.52% | 4.16% | 5.94% | 15.14% |
| Calculated: | 61.16% | 4.28% | 5.94% | 15.04% |

EXAMPLE 27

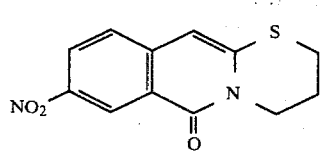

To 20 ml. of o-dichlorobenzene were added 2.2 g. of 2-carboxymethylbenzoic acid, 0.82 g. of sodium acetate, and 1.72 g. of 3-aminopropanethiol hydrobromide. After heating the mixture to 140°–150° C. for 2 hours, 1.9 g. of p-toluenesulfonic acid was added thereto, and the resultant mixture was heated to the same temperature as above for one hour. Then, after cooling the reaction mixture, the solvent was distilled off under reduced pressure and after adding water to the residue obtained, the product was extracted twice each time with 50 ml. of chloroform. The extracts were combined with each other, washed with water and then a diluted aqueous sodium carbonate solution, and dried over anhydrous sodium sulfate. The solvent was distilled off under reduced pressure and the residue obtained was applied to a silica gel column chromatography and purified using chloroform as an eluting solution. The crude crystals (700 mg.) thus obtained were further recrystallized from ethyl acetate to provide 500 mg. of 8-nitro-6-oxo-3,4-dihydro-2H,6H-1,3-thiazino[3,2-b]isoquinoline.

Melting point 224°–226° C.

Elemental analysis for $C_{12}H_{10}N_2O_3S$:

|  | C | H | N | S |
|---|---|---|---|---|
| Found: | 54.60% | 3.93% | 10.50% | 11.92% |
| Calculated: | 54.95% | 3.84% | 10.68% | 12.22% |

EXAMPLE 28

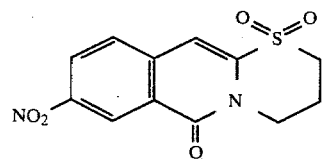

A mixture of 300 mg. of 8-nitro-6-oxo-3,4-dihydro-2H,6H-1,3-thiazino[3,2-b]isoquinoline, 0.26 ml. of a 35% aqueous hydrogen peroxide solution, and 5 ml. of acetic acid was refluxed for 1.5 hours. After the reaction was over, the reaction mixture was cooled and the precipitates formed were recovered by filtration, washed with water, and dried. By recrystallizing the product from acetic acid, 190 mg. of 8-nitro-6-oxo-3,4-dihydro-2H,6H-1,3-thiazino[3,2-b]isoquinoline-1,1-dioxide was obtained.

Melting point 242°–244° C.

Elemental analysis for $C_{12}H_{10}N_2O_5S$:

|  | C | H | N | S |
|---|---|---|---|---|
| Found: | 48.65% | 3.32% | 9.39% | 10.70% |
| Calculated: | 48.97% | 3.40% | 9.52% | 10.88% |

EXAMPLE 29

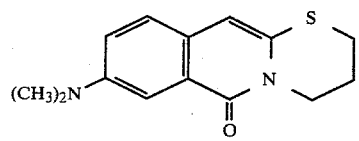

To 20 ml. of o-dichlorobenzene were added 2.3 g. of 2-carboxymethyl-5-dimethylaminobenzoic acid, 0.9 g. of sodium acetate, and 1.8 g. of 3-aminopropanethiol hydrobromide and after heating the mixture to 140°–150° C. for 2 hours and adding thereto 2.7 g. of p-toluenesulfonic acid, the resultant mixture was heated to the same temperature as above for one hour. Then, the reaction mixture was cooled and then the solvent was distilled off under reduced pressure. After adding water to the residue, it was extracted twice each time with 50 ml. of chloroform. The extracts were combined with each other, washed with water, and dried over anhydrous magnesium sulfate. Thereafter, chloroform was distilled off under reduced pressure and the residue formed was applied to a silica gel column chromatography and purified using chloroform as an eluting solution. The crude crystals obtained were further recrystallized from cyclohexane to provide 400 mg. of 8-dimethylamino-6-oxo-3,4-dihydro-2H,6H-1,3-thiazino[3,2-b]isoquinoline.

Melting point 141°–142° C.

Elemental analysis for $C_{14}H_{16}N_2OS$:

|  | C | H | N | S |
|---|---|---|---|---|
| Found: | 64.44% | 6.20% | 10.61% | 12.75% |
| Calculated: | 64.59% | 6.19% | 10.76% | 12.32% |

EXAMPLE 30

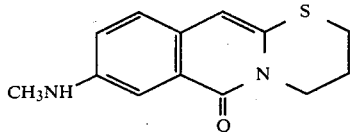

By following the same procedure as in Example 29 using 2.3 g. of 2-carboxymethyl-5-methylaminobenzoic acid and 1.8 g. of 3-aminopropanethiol.hydrobromide, 300 mg. of 8-methylamino-6-oxo-3,4-dihydro-2H,6H-1,3-thiazino[3,2-b]isoquinoline was obtained.

Melting point 171°–172° C.

Elemental analysis for $C_{13}H_{14}N_2OS$:

|  | C | H | N | S |
|---|---|---|---|---|
| Found: | 63.28% | 5.72% | 11.27% | 12.80% |
| Calculated: | 63.39% | 5.73% | 11.37% | 13.02% |

EXAMPLE 31

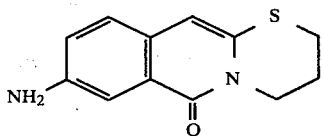

Hydrogen gas was blown into a mixture of 0.5 g. of 8-nitro-6-oxo-3,4-dihydro-2H,6H-1,3-thiazino[3,2-b]isoquinoline, 100 mg. of 5% pd/c, and 20 ml. of chloroform. After the absorption of hydrogen gas stopped, the reaction mixture was filtered and the filtrate was distilled under reduced pressure. The residue formed was recrystallized from benzene-hexane to provide 170 mg. of 8-amino-6-oxo-3,4-dihydro-2H,6H-1,3-thiazino[3,2-b]isoquinoline.

Melting point 151°–152° C.

Elemental analysis for $C_{12}H_{12}N_2OS$:

|  | C | H | N | S |
|---|---|---|---|---|
| Found: | 62.01% | 5.27% | 12.05% | 13.75% |
| Calculated: | 62.04% | 5.21% | 12.06% | 13.80% |

EXAMPLE 32

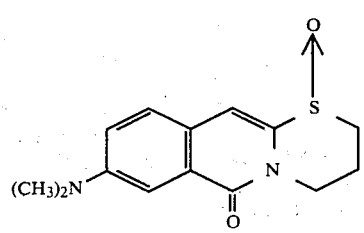

A mixture of 550 mg. of 8-dimethylamino-6-oxo-3,4-dihydro-2H,6H-1,3-thiazino[3,2-b]isoquinoline, 10 ml. of acetic acid, and 0.41 ml. of a 35% aqueous hydrogen peroxide solution was stirred at 20°–30° C. After one hour, the reaction mixture was filtered and after adding 10 ml. of water to the filtrate, anhydrous sodium carbonate was added to it to make the filtrate basic. The precipitates formed were recovered by filtration and dried. By recrystallizing from benzene-hexane, 300 mg. of 8-dimethylamino-6-oxo-3,4-dihydro-2H,6H-1,3-thiazino[3,2-b]isoquinoline-1-oxide was obtained.

Melting point 190°–192° C.

Elemental analysis for $C_{14}H_{16}N_2O_2S$:

|  | C | H | N | S |
|---|---|---|---|---|
| Found: | 61.09% | 5.88% | 9.95% | 11.80% |
| Calculated: | 60.85% | 5.84% | 10.14% | 11.60% |

EXAMPLE 33

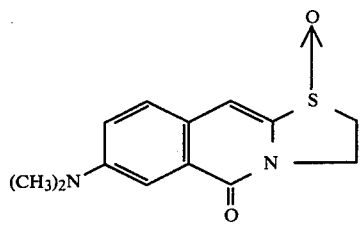

In 2 ml. of acetic acid was dissolved 250 mg. of 7-dimethylamino-5-oxo-2,3-dihydro-5H-thiazolo[3,2-b]isoquinoline followed by cooling and after adding 0.1 ml. of a 35% aqueous hydrogen peroxide solution to the solution, the resultant mixture was stirred for 20 hours at room temperature. After the reaction was over, the reaction mixture obtained was poured in ice water and after making the reaction mixture alkaline with sodium carbonate, the product was extracted twice each time with 50 ml. of ethyl acetate. The extracts were combined with each other, washed with water, and dried. The solvent was distilled off under reduced pressure and the residue obtained was recrystallized from benzene hexane to provide 80 mg. of 7-dimethylamino-5-oxo-2,3-dihydro-5H-thiazolo[3,2-b]isoquinoline-1-oxide.

Elemental analysis for $C_{13}H_{14}N_2O_2S$:

|  | C | H | N | S |
|---|---|---|---|---|
| Found: | 59.44% | 5.30% | 10.30% | 11.99% |
| Calculated: | 59.52% | 5.38% | 10.68% | 12.22% |

EXAMPLE 34

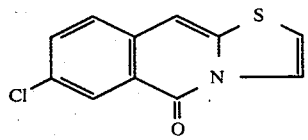

In 12 ml. of acetic anhydride were dissolved 1.0 g of 7-chloro-5-oxo-2,3-dihydro-5H-thiazolo[3,2-b]isoquinoline-1-oxide and a small amount of anhydrous sodium acetate and the solution thus formed was refluxed for 12 hours. The reaction solvent was distilled off under reduced pressure and after adding to the solid residue thus formed 12 ml. of concentrated sulfuric acid, the mixture was allowed to stand for 30 minutes. The reaction mixture was poured in ice water and the crystals precipitated were recovered by filtration and recrystallized from a mixture of cyclohexane and ethyl acetate (4:1 by volume ratio) to provide 380 mg. of 7-chloro-5-oxo-5H-thiazolo[3,2-b]isoquinoline.

Melting point 172°–173° C.

Elemental analysis for $C_{11}H_6NOSCl$:

|  | C | H | N | S | Cl |
|---|---|---|---|---|---|
| Found: | 55.83% | 2.37% | 5.79% | 13.32% | 15.34% |
| Calculated: | 56.06% | 2.57% | 5.94% | 13.60% | 15.04% |

EXAMPLE 35

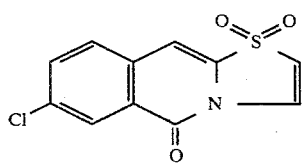

To 5 ml. of glacial acetic acid containing 300 mg. of 7-chloro-5-oxo-5H-thiazolo[3,2-b]isoquinoline was added 3.5 ml. of a 35% aqueous hydrogen peroxide solution and the mixture was refluxed for 2 hours with stirring. The reaction mixture was poured into ice water and the solids precipitated were recovered by filtration and recrystallized from ethyl acetate to provide 100 mg. of 7-chloro-5-oxo-5H-thiazolo[3,2-b]isoquinoline-1,1-dioxide.

Melting point 254°–255° C.

Elemental analysis for $C_{11}H_6NO_3SCl$:

|  | C | H | N | S | Cl |
|---|---|---|---|---|---|
| Found: | 49.18% | 2.08% | 5.18% | 11.95% | 13.48% |
| Calculated: | 49.36% | 2.26% | 5.23% | 11.98% | 13.24% |

EXAMPLE 36

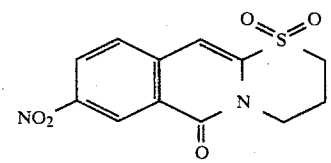

While ice-cooling 10 ml. of fuming nitric acid, 2.0 g. of 6-oxo-3,4-dihydro-2H,6H-1,3-thiazino[3,2-b]isoquinoline-1,1-dioxide was added thereto slowly so that the reaction temperature was not over 6° C. After the reaction was over, the reaction product was poured into ice water and extracted twice each time with 50 ml. of chloroform. The extract was washed with water and a diluted aqueous sodium carbonate solution, and then dried over anhydrous magnesium sulfate. The solvent was distilled off to provide 430 mg. of a crude product. The product was recrystallized from acetic acid to provide 160 mg. of 8-nitro-6-oxo-3,4-dihydro-2H,6H-1,3-thiazino[3,2-b]isoquinoline-1,1-dioxide.

Melting point 242°–244° C.

EXAMPLE 37

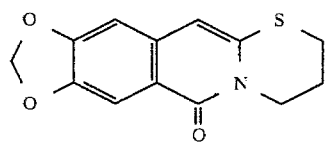

In 10 ml. of o-dichlorobenzene were dissolved 1.5 g. of 5-carboxy-6-carboxymethyl-1,3-benzodioxole and 1.5 g. of 3-aminopropanethiol hydrobromide and after adding 0.72 g. of anhydrous sodium acetate to the solution, the resultant mixture was heated to 150°–160° C. for 2 hours with stirring. Then, 1.2 g. of p-toluenesulfonic acid was added to the mixture at 150°–160° C. followed by stirring for 30 minutes. The reaction mixture obtained was cooled to room temperature and the solids precipitated were recovered by filtration and washed with 30 ml. of benzene. The filtrate was combined with the washings and the mixture was distilled under reduced pressure. The solid residue formed was recrystallized from isopropanol to provide 1.5 g. of 6-oxo-3,4-dihydro-2H,6H-1,3-dioxolo[g][1,3]-thiazino[3,2-b]isoquinoline.

Melting point 121°–122° C.

Elemental analysis for $C_{13}H_{11}NO_3S$:

|  | C | H | N | S |
|---|---|---|---|---|
| Found: | 59.39% | 4.40% | 5.07% | 11.94% |
| Calculated: | 59.76% | 4.24% | 5.36% | 12.27% |

EXAMPLE 38

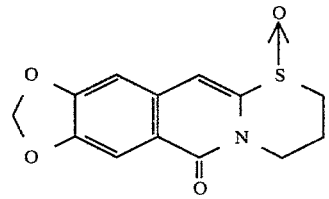

In 7 ml. of glacial acetic acid was dissolved 650 mg. of 6-oxo-3,4-dihydro-2H,6H-1,3-dioxolo[g][1,3]-thiazino[3,2-b]isoquinoline and after adding 0.24 ml. of a 35% aqueous hydrogen peroxide solution to the solution under ice-cooling, the resultant mixture was allowed to stand overnight at room temperature. The reaction mixture was poured in ice water and then neutralized with sodium carbonate. The solids precipitated were recovered by filtration and recrystallized, after washing with water, from ethanol to provide 430 mg. of 6-oxo-3,4-dihydro-2H,6H-1,3-dioxolo[g][1,3]-thiazino[3,2-b]isoquinoline-1-oxide.

Melting point 189°–190° C.

Elemental analysis for $C_{13}H_{11}NO_4S$:

|  | C | H | N | S |
|---|---|---|---|---|
| Found: | 56.69% | 3.89% | 4.62% | 11.31% |
| Calculated: | 56.31% | 4.00% | 5.05% | 11.56% |

EXAMPLE 39

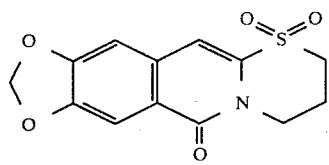

In 10 ml. of glacial acetic acid was dissolved 520 mg. of 6-oxo-3,4-dihydro-2H,6H-1,3-dioxolo[g][1,3]-thiazino[3,2-b]isoquinoline and after adding 0.4 ml. of a 35% aqueous hydrogen peroxide solution to the solution, the resultant mixture was heated to 70°–80° C. for 3 hours.

The reaction mixture obtained was poured into ice water and neutralized with sodium carbonate. The solids precipitated were recovered by filtration, washed with water, and recrystallized from glacial acetic acid to provide 100 mg. of 6-oxo-3,4-dihydro-2H,6H-1,3-dioxolo[g][1,3]-thiazino[3,2-b]isoquinoline-1,1-dioxide.

Melting point 261°–262° C.

Elemental analysis for $C_{13}H_{11}NO_5S$:

|  | C | H | N | S |
|---|---|---|---|---|
| Found: | 52.83% | 3.76% | 4.82% | 10.86% |
| Calculated: | 53.24% | 3.78% | 4.78% | 10.93% |

EXAMPLE 40

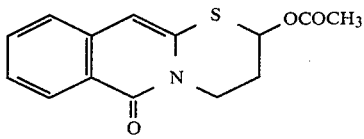

A mixture of 1.5 g. of 6-oxo-3,4-dihydro-2H,6H-1,3-thiazino[3,2-b]isoquinoline-1-oxide, 20 ml. of acetic anhydride, and 100 mg. of sodium acetate was refluxed for 10 hours. After cooling, the reaction mixture was poured into 80 ml. of ice-water and extracted twice each time with 50 ml. of ethyl acetate. The extracts were combined with each other, washed with a diluted aqueous sodium carbonate solution and then water, dried over anhydrous sodium sulfate, and then the solvent was distilled off under reduced pressure. The residue obtained was applied to a silica gel column chromatography and purified using chloroform as an eluting solution to provide 1.23 g. of oily 2-acetoxy-6-oxo-3,4-dihydro-2H,6H-1,3-thiazino[3,2-b]isoquinoline.

Elemental analysis for $C_{14}H_{13}NO_3S$:

|  | C | H | N | S |
|---|---|---|---|---|
| Found: | 60.89% | 4.94% | 4.92% | 11.52% |
| Calculated: | 61.07% | 4.76% | 5.09% | 11.65% |

EXAMPLE 41

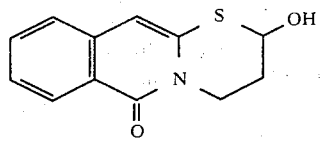

A mixture of 500 mg. of 2-acetoxy-6-oxo-3,4-dihydro-2H,6H-1,3-thiazino[3,2-b]isoquinoline, 4ml. of methanol, and 1 ml. of a 1 N aqueous sodium hydroxide solution was stirred for 30 minutes at room temperature. Then, the reaction mixture obtained was poured into 30 ml. of ice water, neutralized with diluted hydrochloric acid, and extracted twice each time with 30 ml. of ethyl acetate. The extracts were combined with each other, washed with water, dried over anhydrous sodium sulfate, and then the solvent was distilled off under reduced pressure. Thereafter, 300 mg. of the residue obtained was recrystallized from ethyl acetate n-hexane to provide 100 mg. of 2-hydroxy-6-oxo-3,4-dihydro-2H,6H-1,3-thiazino[3,2-b]isoquinoline.

Melting point 175°–180° C.

Elemental analysis for $C_{12}H_{11}NO_2S$:

|  | C | H | N | S |
|---|---|---|---|---|
| Found: | 61.66% | 4.72% | 5.69% | 13.73% |
| Calculated: | 61.78% | 4.75% | 6.00% | 13.74% |

EXAMPLE 42

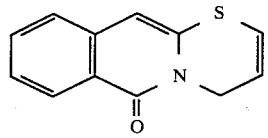

A mixture of 1.4 g. of 2-acetoxy-6-oxo-3,4-dihydro-2H,6H-1,3-thiazino[3,2-b]isoquinoline, 45 mg. of p-toluenesulfonic acid, and 15 ml. of o-dichlorobenzene was heated to 140°–160° C. for 2 hours. After cooling the reaction mixture the solvent was distilled off from the reaction mixture under reduced pressure and the residue formed was dissolved in 100 ml. of ethyl acetate. The ethyl acetate solution was washed with water, dried over anhydrous sodium sulfate, and then the solvent was distilled off under reduced pressure. The residue obtained was applied to a silica gel column chromatography, purified using chloroform as an eluting solution recrystallized from cyclohexane to provide 600 mg. of 6-oxo-4H,6H-1,3-thiazino[3,2-b]isoquinoline.

Melting point 127°–128° C.

Elemental analysis for $C_{12}H_9NOS$:

|  | C | H | N | S |
|---|---|---|---|---|
| Found: | 66.55% | 4.24% | 6.27% | 14.49% |
| Calculated: | 66.95% | 4.21% | 6.51% | 14.89% |

EXAMPLE 43

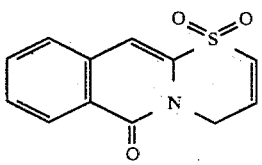

A mixture of 250 mg. of 6-oxo-4H,6H-1,3-thiazino[3,2-b]isoquinoline, 3 ml. of acetic acid, and 0.2 ml. of a 35% aqueous hydrogen peroxide solution was heated to 90°–100° C. for 2 hours. After cooling, the reaction mixture obtained was poured into 50 ml. of ice water to deposit precipitates. The precipitates were recovered by filtration and recrystallized from ethyl acetate ethanol to provide 180 mg. of 6-oxo-4H,6H-1,3-thiazino[3,2-b]isoquinoline.

Melting point higher than 260° C. (decomp.)
Elemental analysis for $C_{12}H_9NO_3S$:

|  | C | H | N | S |
|---|---|---|---|---|
| Found: | 58.34% | 3.60% | 5.56% | 13.01% |
| Calculated: | 58.29% | 3,67% | 5,66% | 12.97% |

EXAMPLE 44

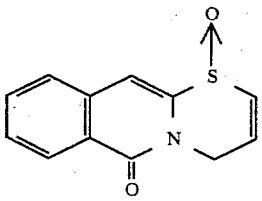

In 2 ml. of acetic acid was dissolved 200 mg. of 6-oxo-4H,6H-1,3-thiazino[3,2-b]isoquinoline and after cooling the solution and adding 0.1 ml. of a 35% aqueous hydrogen peroxide solution to the solution, the resultant mixture was stirred one day at room temperature. After the reaction was over, the reaction mixture was poured into 30 ml. of ice water and extracted twice each time with 30 ml. of ethyl acetate. The extracts were combined with each other, washed with a diluted aqueous sodium carbonate solution and then water, dried over anhydrous sodium sulfate, and then the solvent was distilled off under reduced pressure. The resiude obtained was applied to a silica gel column chromatography, purified using chloroform as an eluting solution and recrystallized from ethanol to provide 49 mg. of 6-oxo-4H,6H-1,3-thiazino[3,2-b]isoquinoline.

Melting point 161°–163° C.
Elemental analysis for $C_{12}H_9NO_2S$:

|  | C | H | N | S |
|---|---|---|---|---|
| Found: | 62.32% | 3.92% | 6.06% | 13.86% |
| Calculated: | 62.17% | 4.03% | 5.94% | 14.10% |

EXAMPLE 45

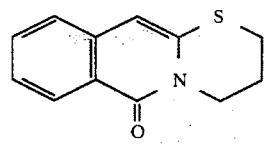

(a-1). A mixture of 1.6 g. of homophthalic anhydride, 2.19 g. of 3-aminopropyl bromide.hydrobromide, 0.82 g. of sodium acetate, and 10 ml. of o-dichlorobenzene was refluxed for 1.5 hours. After cooling, the solvent was distilled off from the reaction mixture obtained under reduced pressure. The residue formed was applied to a silica gel column chromatography and purified using chloroform as an eluting solution to provide 1.3 g. of oily N-(3-bromopropyl)homophthalimide.

Nuclear magnetic resonance spectra (CDCl$_3$): δ: 2.2 (2H, m), 3.4 (2H,t), 4.0 (2H, S), 4.1 (2H, t), 7.2–8.2 (4H, m).

(a-2). A mixture of 1.8 g. of 2-carboxymethylbenzoic acid, 2.19 g. of 3-aminopropyl bromide.hydrobromide, 0.82 g. of sodium acetate, and 10 ml. of o-dichlorobenzene was heated to 110°–170° C. for 3 hours. After cooling the reaction mixture, the precipitates formed were filtered off from the reaction mixture and then the solvent was distilled off from the filtrate under reduced pressure. The residue formed was extracted with 50 ml. of ethyl acetate. The extract was successively treated with a diluted aqueous sodium carbonate solution, diluted hydrochloric acid, and water, dried over anhydrous sodium sulfate, and then the solvent was distilled off under reduced pressure. The residue obtained was applied to a silica gel column chromatography and purified using chloroform as an eluting solution to provide 400 mg. of oily N-(3-bromopropyl)homophthalimide.

(b). After blowing hydrogen sulfide gas into a mixture of 1 g. of potassium hydroxide, 6 ml. of ethanol, and 5 ml. of water for 45 minutes, 1.3 g. of N-(3-bromopropyl)homophthalimide was added to the mixture while further blowing hydrogen sulfide gas at 5°–10° C. and then the solution was stirred for 3 hours at room temperature. After the reaction was over, the reaction mixture was poured into 50 ml. of cold water and extracted with 100 ml. of chloroform. The extract was dried over anhydrous sodium sulfate and then the solvent was distilled off under reduced pressure. The residue obtained was applied to a silica gel column chromatography and purified using a mixture of benzene and chloroform (1:1 by volume ratio) as an eluting solution to provide 400 mg. of oily N-(3-mercaptopropyl)homophthalimide.

Nuclear magnetic resonance spectra (CDCl$_3$): δ: 1,44–1.62(1H,t), 1.8–2.04(2H,m), 2.4–2.6(2H,m), 4.0–4.8(2H, t), 4.02(2H, s), 7.2–8.22(2H, m).

(c). A mixture of 112 mg. of N-(3-mercaptopropyl)homophthalimide, 172 mg. of p-toluenesulfonic acid, and 4 ml. of o-dichlorobenzene was heated to 120° C. for 30 minutes. After cooling the reaction mixture, the solvent was distilled off from the reaction mixture under reduced pressure and the residue obtained was extracted with 50 ml. of benzene. The extract was washed with water, dried over anhydrous sodium sulfate, and then the solvent was distilled off under reduced pressure. By recrystallizing the residue thus obtained from isopropyl alcohol, 70 mg. of 6-oxo-3,4-dihydro-2H,6H-1,3-thiazino[3,2-b]isoquinoline was obtained.

EXAMPLE 46

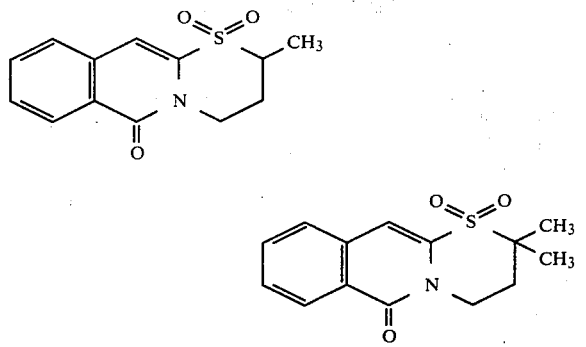

To 50 ml. of liquid ammonia were added 520 mg. of metallic potassium and 15 mg. of ferric nitrate and after stirring the mixture for 5 minutes to form potassium amide, 1.5 g. of 6-oxo-3,4-dihydro-2H,6H-1,3-thiazino[3,2-b]isoquinoline-1,1-dioxide was added to the mixture followed by stirring for 15 minutes. Then, 2 g. of methyl iodide was added to the mixture under cooling followed by stirring for 5 minutes and the reaction temperature raised gradually to room temperature to evaporate of liquid ammonia. Then, the reaction mixture was extracted with 100 ml. of chloroform and the extract was washed with diluted hydrochloric acid and dried over anhydrous sodium sulfate. Thereafter, the solvent was distilled off under reduced pressure. The residue formed was applied to a silica gel column chromatography and purified using a mixture of benzene and chloroform (1:1 by volume ratio) as an eluting solution to provide two kinds of products.

The product obtained from the first product fraction was recrystallized further from benzene n-hexane to provide 200 mg. of 2,2-dimethyl-6-oxo-3,4-dihydro-2H,6H-1,3-thiazino[3,2-b]isoquinoline-1,1-dioxide.

Melting point 185°–186° C.

Elemental analysis for $C_{14}H_{15}NO_3S$:

|  | C | H | N | S |
|---|---|---|---|---|
| Found: | 60.21% | 5.29% | 4.77% | 11.56% |
| Calculated: | 60.63% | 5.45% | 5.05% | 11.56% |

Then, the product obtained from the following fraction was recrystallized from benzene to provide 700 mg. of 2-methyl-6-oxo-3,4-dihydro-2H,6H-1,3-thiazino[3,2-b]isoquinoline-1,1-dioxide.

Melting point 215°–217° C.

Elemental analysis for $C_{13}H_{13}NO_3S$:

|  | C | H | N | S |
|---|---|---|---|---|
| Found: | 59.09% | 4.98% | 5.49% | 12.20% |
| Calculated: | 59.30% | 4.98% | 5.32% | 12.18% |

EXAMPLE 47

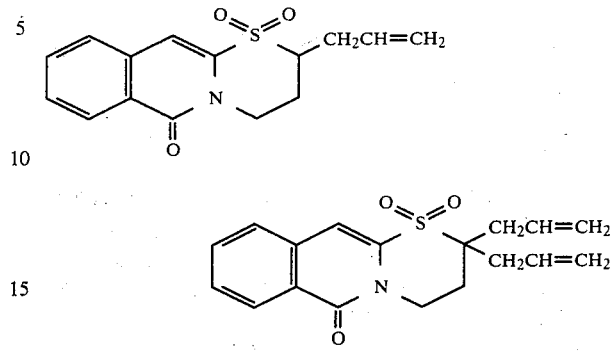

To 40 ml. of liquid ammonia were added 420 mg. of metallic potassium and 10 mg. of ferric nitrate and the mixture was stirred for 5 minutes to provide potassium amide. Then, 1.5 g. of 6-oxo-3,4-dihydro-2H,6H-1,3-thiazino[3,2-b]isoquinoline-1,1-dioxide was added to the mixture followed by stirring for 15 minutes. After further adding 1.3 g. of allyl bromide to the reaction mixture under cooling followed by stirring for 5 minutes, the reaction temperature was raised gradually to room temperature to evaporate liquid ammonia. Thereafter, the reaction product was extracted with 100 ml. of chloroform and the extract was washed with diluted hydrochloric acid, dried over anhydrous sodium sulfate, and then the solvent was distilled off under reduced pressure. The residue formed was applied to a silica gel column chromatography and purified using chloroform as an eluting solution to provide two kinds of products. The product obtained from the first product fraction was recrystallized further from benzene-cyclohexane to provide 100 mg. of 2,2-diallyl-6-oxo-3,4-dihydro-2H,6H-1,3-thiazino[3,2-b]isoquinoline-1,1-dioxide.

Melting point 100°–101° C.

Elemental analysis for $C_{18}H_{19}NO_3S$:

|  | C | H | N | S |
|---|---|---|---|---|
| Found: | 65.56 | 5.89% | 4.10% | 9.71% |
| Calculated: | 65.57% | 5.77% | 4.25% | 9.71% |

Then, the product obtained from the following fraction was further recrystallized from cyclohexane to provide 140 mg. of 2-allyl-6-oxo-3,4-dihydro-2H,6H-1,3-thiazino[3,2-b]isoquinoline-1,1-dioxide.

Melting point 144°–146° C.

Elemental analysis for $C_{15}H_{15}NO_3S$:

|  | C | H | N | S |
|---|---|---|---|---|
| Found: | 62.01% | 5.06% | 4.89% | 11.10% |
| Calculated: | 62.23% | 5.18% | 4.84% | 11.06% |

EXAMPLE 48

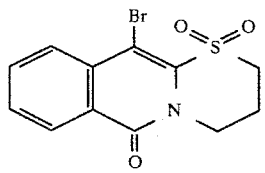

A mixture of 2.5 g. of 6-oxo-3,4-dihydro-2H,6H-1,3-thiazino[3,2-b]isoquinoline-B 1,1-dioxide and 10 ml. of acetic acid was heated to 80°–90° C. and after adding dropwise a mixture of 1.8 g. of bromine and 5 ml. of acetic acid to the mixture, the resultant mixture was heated to 80°–90° C. for 4 hours. After cooling, the precipitates formed were recovered by filtration and recrystallized from acetic acid to provide 1.2 g. of 11-bromo-6-oxo-3,4-dihydro-2H,6H-1,3-thiazino[3,2-b]isoquinoline-1,1-dioxide.

Melting point 240°–250° C. (decompd.)
Elemental analysis for $C_{12}H_{10}NO_3SBr$:

|  | C | H | N | S | Br |
|---|---|---|---|---|---|
| Found: | 43.71% | 3.00% | 4.50% | 9.60% | 24.21% |
| Calculated: | 43.90% | 3.04% | 4.26% | 9.76% | 24.39% |

EXAMPLE 49

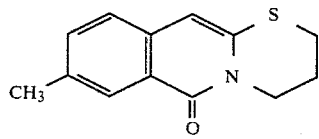

A mixture of 0.8 g. of 2-carboxymethyl-5-methylbenzoic acid, 0.72 g. of 3-aminopropanethiol.hydrobromide, 0.34 g. of sodium acetate, and 10 ml. of o-dichlorobenzene was heated to 150°–160° C. for 2 hours. Then, 0.8 g. of p-toluenesulfonic acid was added thereto and the mixture was heated to 150°–160° C., for one hour. After cooling, the reaction mixture was filtered and then the solvent was diltilled off under reduced pressure from the filtrate. The residue formed was dissolved in 850 ml. of benzene.

Thereafter, the solution was successively washed with a diluted aqueous sodium carbonate solution and water, dried over anhydrous magnesium sulfate, and then the solvent was distilled off under reduced pressure. The residue obtained was recrystallized from cyclohexane to provide 400 mg. of 8-methyl-6-oxo-3,4-dihydro-2H,6H-1,3-thiazino[3,2-b]isoquinoline.

Melting point 89°–90° C.
Elemental analysis for $C_{13}H_{13}NSO$:

|  | C | H | N | S |
|---|---|---|---|---|
| Found: | 67.79% | 5.70% | 5.75% | 13.77% |
| Calculated: | 67.50% | 5.66% | 6.06% | 13.86% |

EXAMPLE 50

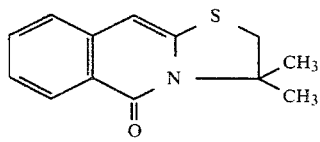

By following the same procedure as in Example 49 using a mixture of 240 mg. of 2-carboxymethylbenzoic acid, 300 mg. of 2-amino-2-methylpropanethiol, 164 mg. of sodium acetate, and 5 ml. of o-dichlorobenzene, 120 mg. of 3,3-dimethyl-5-oxo-2,3-dihydro-5H-thiazolo[3,2-b]isoquinoline was obtained.

Melting point 95°–96° C. (recrystallized from n-hexane)
Elemental analysis for $C_{13}H_{13}NSO$:

|  | C | H | N | S |
|---|---|---|---|---|
| Found: | 67.34% | 5.60% | 5.72% | 13.75% |
| Calculated: | 67.50% | 5.66% | 6.06% | 13.86% |

EXAMPLE 51

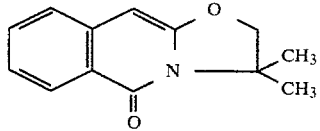

A mixture of 1 g. of 2-carboxymethylbenzoic acid, 0.5 g. of 2-amino-2-methylpropanol, and 5 ml. of o-dichlorobenzene was heated to 150°–160° C. for 4 hours. After cooling, the solvent was distilled off from the reaction mixture under reduced pressure and the residue obtained was dissolved in 30 ml. of ethyl acetate. Then, the solution was successively wased with diluted hydrochloric acid, a diluted sodium carbonate solution, and water, dried over anhydrous magnesium sulfate, and then the solvent was distilled off under reduced pressure. By recrystallizing the residue obtained from cyclohexane, 700 mg. of 3,3-dimethyl-5-oxo-2,3-dihydro-5H-oxazolo[3,2-b]isoquinoline was obtained.

Melting point 91°–92° C.
Elemental analysis for $C_{13}H_{13}NO_2$:

|  | C | H | N |
|---|---|---|---|
| Found: | 72.21% | 6.03% | 6.65% |
| Calculated: | 72.54% | 6.09% | 6.51% |

EXAMPLE 52

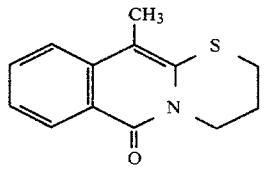

A mixture of 0.5 g. of α-methyl-2-carboxymethylbenzoic acid, 0.5 g. of 3-aminopropanethiol hydrobromide, 0.25 g. of sodium acetate and 3 ml. of o-dichlorobenzene was heated to 140°-150° C. for one hour with stirring. The reaction mixture obtained was cooled below 100° C. and after adding thereto 0.6 g. of p-toluensulfonic acid, the mixture was heated to 140°-150° C. for one hour. After cooling, 15 ml. of chloroform was added to the reaction mixture, then the mixture obtained was successively washed with 15 ml. of water and 15 ml. of 10% aqueous potassium carbonate solution. The chloroform solution obtained was dried over anhydrous sodium sulfate and then the solvent was distilled off under reduced pressure. The crystalline residue was applied to a silica gel column chromatography, purified using chloroform as an eluting solution, and further recrystallized from ethanol to provide 0.38 g. of 11-methyl-6-oxo-3,4-dihydro-2H,6H-1,3-thiazino[3,2-b]isoquinoline.

Melting point 96°-98° C.

Elemental analysis for $C_{13}H_{13}NOS$

|  | C | H | N |
|---|---|---|---|
| Found: | 67.13% | 5.73% | 5.75% |
| Calculated: | 67.50% | 5.66% | 6.06% |

EXAMPLE 53

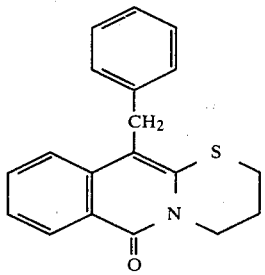

By following the same procedure as in Example 52 using 0.8 g. of α-benzyl-z-carboxymethylbenzoic acid 0.55 g. of 3-aminopropanethiol.hydrobromide, 0.27 g. of sodium acetate and 0.9 g. of p-toluenesulfonic acid, 6.63 g. of 11-benzyl-6-oxo-3,4-dihydro-2H,6H-1,3-thiazino[3,2-b]isoquinoline.

Melting point 118°-119° C. (recrystallized from ethanol).

Elemental analysis for $C_{19}H_{17}NSO$:

|  | C | H | N |
|---|---|---|---|
| Found: | 74.01% | 5.55% | 4.56% |
| Calculated: | 74.24% | 5.57% | 4.56% |

EXAMPLE 54

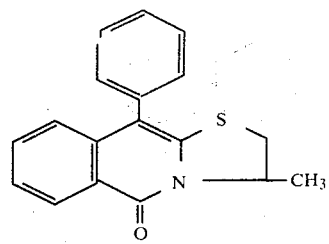

By following the same procedure as in Example 52 using 0.3 g. of α-phenyl-2-carboxymethylbenzoic acid, 0.18 g. of 2-aminopropanethiol.hydrochloride, 0.12 g. of sodium acetate, and 0.3 g. of p-toluenesulfonic acid, 0.16 g. of 3-methyl-5-oxo-10-phenyl-2,3-dihydro-5H-thiazolo[3,2-b]isoquinoline was obtained.

Melting point 204°-208° C. (recrystallized from ethanol).

Elemental analysis for $C_{18}H_{15}NSO$:

|  | C | H | N |
|---|---|---|---|
| Found: | 73.46% | 5.22% | 4.81% |
| Calculated: | 73.69% | 5.15% | 4.77% |

EXAMPLE 55

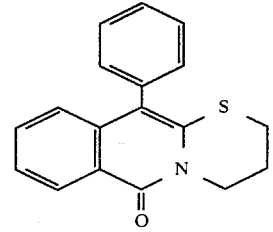

By following the same procedure as in Example 52 using 0.7 g. of α-phenyl-2-carboxymethylbenzoic acid, 0.58 g. of 3-aminopropanethiol.hydrobromide, 0.3 g. of sodium acetate and 0.75 g. of p-toluenesulfonic acid, 0.54 g. of 6-oxo-11-phenyl-3,4-dihydro-2H,6H[1,3]thiazino[3,2-b] isoquinoline was obtained.

Melting point 234°-235° C. (recrystallized from ethanol)

Elemental analysis for $C_{18}H_{15}NSO$:

|  | C | H | N |
|---|---|---|---|
| Found: | 73.52% | 5.14% | 4.62% |
| Calculated: | 73.69% | 5.15% | 4.77% |

EXAMPLE 56

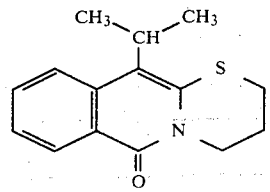

A mixture of 0.2 g. of α-isopropyl-2-carboxymethylbenzoic acid, 0.2 g. of 3-aminopropane thiol.hydrobromide, 0.1 g. of sodium acetate, and 3 ml. of o-dichlorobenzene was heated to 140°–150° C. for one hour with stirring. The reaction mixture obtained was cooled below 100° C. and after adding thereto 0.25 g. of p-toluenesulfonic acid, the mixture was heated to 160° C. for 6 hours. Thereafter, by following the same procedure as in Example 52, 0.07 g. of 11-isopropyl-6-oxo-3,4-dihydro-2H,6H-1,3-thiazino[3,2-b]isoquinoline was obtained.

Melting point 123°–124° C. (recrystallized from aqueous methanol).

Elemental analysis for $C_{15}H_{17}NOS$:

|  | C | H | N |
|---|---|---|---|
| Found: | 69.02% | 6.49% | 5.18% |
| Calculated: | 69.46% | 6.61% | 5.40% |

EXAMPLE 57

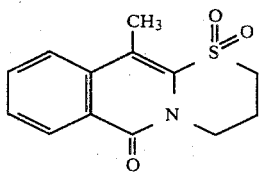

In 2 ml. of acetic acid was dissolved 0.2 g. of 11-methyl-6-oxo-3,4-dihydro-2H,6H-1,3-thiazino[3,2-b]isoquinoline and after adding 0.25 g. of a 30% aqueous hydrogen peroxide solution to the solution, the resultant mixture was heated to 80°–100° C. for 2 hours. The reaction mixture obtained was dispersed in 20 ml. of water and the crystals precipitated were recovered by filtration and recrystallized from ethanol to provide 0.08 g. of 11-methyl-6-oxo-3,4-dihydro-2H,6H-1,3-thiazino[3,2-b]isoquinoline-1,1-dioxide.

Melting point 186°–188° C.

Elemental analysis for $C_{13}H_{13}NO_3S$:

|  | C | H | N |
|---|---|---|---|
| Found: | 59.02% | 4.85% | 5.12% |
| Calculated: | 59.30% | 4.98% | 5.32% |

EXAMPLE 58

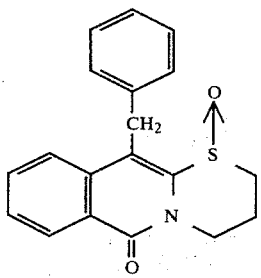

In 2 ml. of acetic acid was dissolved 0.3 g. of 11-benzyl-6-oxo-3,4-dihydro-2H,6H-1,3-thiazino[3,2-b]isoquinoline and after adding thereto 0.13 g. of a 30% aqueous hydrogen peroxide solution, the resultant mixture was allowed to stand for one day. The reaction mixture was dispersed in 20 ml. of water and extracted with 15 ml. of ethyl acetate. The extract was washed with 10 ml. of a 10% aqueous potassium carbonate solution, dried over anhydrous sodium sulfate, and concentrated under reduced pressure. The crystalline residue formed was applied to a silica gel column chromatography, purified using chloroform as an eluting solution and further recrystallized from ethanol to provide 0.18 g. of 11-benzyl-6-oxo-3,4-dihydro-2H,6H-1,3-thiazino[3,2-b]isoquinoline-1-oxide.

Melting point 147°–148° C.

Elemental analysis for $C_{19}H_{17}NSO_2$

|  | C | H | N |
|---|---|---|---|
| Found: | 70.27% | 5.38% | 4.12% |
| Calculated: | 70.56% | 5.30% | 4.33% |

EXAMPLE 59

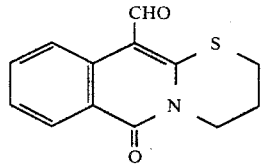

To a mixture of 3 g. of dimethylformamide and 20 ml. of chloroform was added dropwise 3 g. of phosphorus oxychloride with stirring under ice-cooling and then the mixture was allowed to stand for one hour at room temperature. Then, 3 g. of 6-oxo-3,4-dihydro-2H,6H-1,3-thiazino[3,2-b]isoquinoline was added to the solution and the mixture was refluxed for 3 hours. After cooling the reaction mixture, crystals thus precipitated were recovered by filtration, dissolved in 100 ml. of water, and made alkaline with potassium carbonate. The crystals precipitated were recovered by filtration, washed with water, and recrystallized from methanol, after drying, to provide 2.4 g. of 11-formyl-6-oxo-3,4-dihydro-2H,6H-1,3-thiazino[3,2-b]isoquinoline.

Melting point 143°–145° C.

Elemental analysis for $C_{13}H_{11}NO_2S$:

|  | C | H | N |
|---|---|---|---|
| Found: | 63.61% | 4.45% | 5.59% |
| Calculated: | 63.65% | 4.52% | 5.71% |

EXAMPLE 60

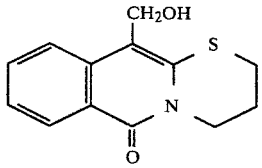

In 20 ml. of methanol was suspended 0.3 g. of 11-formyl-6-oxo-3,4-dihydro-2H,6H-1,3-thiazino[3,2-b]isoquinoline and after adding thereto 50 mg. of sodium borohydride followed by stirring for 10 minutes, the resultant mixture was concentrated under reduced pressure. The residual crystals were recovered, washed with 20 ml. of water, and recrystallized from ethanol after drying to provide 0.25 g. of 11-hydroxymethyl-6-oxo-3,4-dihydro-2H,6H-1,3-thiazino[3,2-b]isoquinoline.

Melting point 166°–168° C.

Elemental analysis for $C_{13}H_{13}NO_2S$:

|  | C | H | N |
|---|---|---|---|
| Found: | 63.00% | 5.26% | 5.87% |
| Calculated: | 63.14% | 5.30% | 5.66% |

EXAMPLE 61

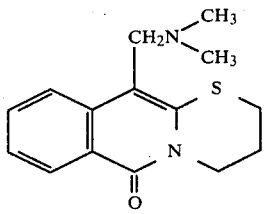

To a solution of 4.5 g. of a 40% aqueous dimethylamine solution, 5 ml. of acetic acid, 3 ml. of 37% aqueous formaldehyde solution, and 20 ml. of ethanol was added 0.7 g. of 6-oxo-3,4-dihydro-2H,6H-1,3-thiazino[3,2-b]isoquinoline and the mixture was refluxed for 16 hours. The reaction mixture formed was concentrated under reduced pressure and after adding 30 ml. of water to the residue, the product was extracted with 20 ml. of ethyl acetate. The ethyl acetate extract was further extracted with 5% hydrochloric acid and after the aqueous extract was made alkaline with potassium carbonate, the aqueous layer was further extracted with 15 ml. of ethyl acetate. The extract was dried over anhydrous sodium sulfate and concentrated under reduced pressure. The residue formed was recrystallized from aqueous ethanol to provide 0.42 g. of 11-dimethylaminomethyl-6-oxo-3,4-dihydro-2H,6H-1,3-thiazino[3,2-b]isoquinoline.½hydrate.

Melting point 62°–64° C.

Elemental analysis for $C_{15}H_{19}N_2O_{3/2}S$:

|  | C | H | N |
|---|---|---|---|
| Found: | 63.23% | 6.76% | 9.69% |
| Calculated: | 63.57% | 6.76% | 9.88% |

EXAMPLE 62

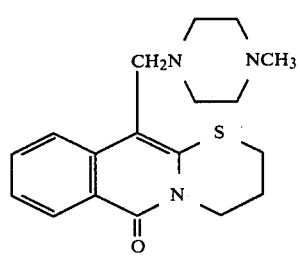

By following the same procedure as in Example 61 using 3.3 g. of 4-methylpiperazine, 6 ml. of acetic acid, 2.5 ml. of a 37% aqueous formaldehyde solution, 20 ml of ethanol, and 0.6 g. of 6-oxo-3,4-dihydro-2H,6H-1,3-thiazino[3,2-b]isoquinoline, crude crystals were obtained. The crude crystals were applied to a silica gel column chromatography, purified using a mixture of chloroform and methanol as an eluting solution, and further recrystallized from ethyl acetate to provide 0.29 g. of 11-[4-methylpiperazinomethyl]-6-oxo-3,4-dihydro-2H,6H-1,3-thiazino[3,2-b]isoquinoline.

Melting point 150°–151° C.

Elemental analysis for $C_{18}H_{23}N_2OS$:

|  | C | H | N |
|---|---|---|---|
| Found: | 65.37% | 7.03% | 12.47% |
| Calculated: | 65.62% | 7.04% | 12.75% |

EXAMPLE 63

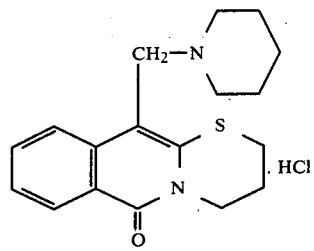

By following the same procedure as in Example 61 using 2.8 g. of piperidine, 4 ml. of acetic acid, 2.5 ml. of a 37% aqueous formaldehyde solution, 20 ml. of ethanol, and 0.6 g. of 6-oxo-3,4-dihydro-2H,6H-1,3-thiazino[3,2-b]isoquinoline, an oily product was obtained. The oily product obtained was applied to a silica gel column chromatography, purified using chloroform as an eluting solution and the oily product obtained was treated with ethanol hydrochloric acid to provide a hydrochloride, which was then recrystallized from methanol-ether to provide 0.2 g. of 11-piperidinomethyl-6-oxo-3,4-dihydro-2H,6H-1,3-thiazino[3,2-b]isoquinoline hydrochloride.

Melting point 221°–223° C.

Elemental analysis for $C_{18}H_{23}N_2ClOS$:

|  | C | H | N |
|---|---|---|---|
| Found: | 61.35% | 6.71% | 7.61% |
| Calculated: | 61.61% | 6.61% | 7.98% |

EXAMPLE 64

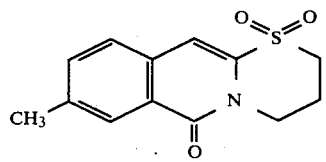

A mixture of 300 mg. of 8-methyl-6-oxo-3,4-dihydro-2H,6H-1,3-thiazino[3,2-b]isoquinoline, 4 ml. of acetic acid, and 0.26 ml. of a 35% aqueous hydrogen peroxide solution was heated to 70°–80° C. for 2 hours. After cooling the reaction mixture, it was poured into ice water and the precipitates formed were recovered by filtration. The precipitates thus obtained were recrystallized from ethyl acetate to provide 200 mg. of 8-methyl- 6-oxo-3,4-dihydro-2H,6H-1,3-thiazino[3,2-b]isoquinoline-1,1-dioxide.

Melting point 219°–221° C.

Elemental analysis for $C_{13}H_{13}NSO_3$:

|  | C | H | N | S |
|---|---|---|---|---|
| Found: | 59.03% | 4.82% | 5.04% | 12.29% |
| Calculated: | 59.30% | 4.98% | 5.32% | 12.18% |

EXAMPLE 65

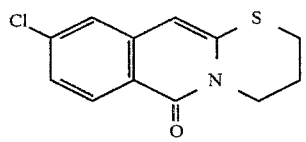

By following the same procedure as in Example 13 using 0.32 g. of 2-carboxymethyl-4-chlorobenzoic acid, 0.37 g. of 3-aminopropanethiol hydrobromide, 0.172 g. of sodium acetate and 0.3 g. of p-toluensulfonic acid, 0.15 g. of 9-chloro-6-oxo-3,4-dihydro-2H,6H-1,3-thiazino[3,2-b]isoquinoline was obtained.

Melting point 109°–110° C. (recrystallized from isopropanol)

Elemental analysis for $C_{12}H_{10}NOSCl$:

|  | C | H | N | S | Cl |
|---|---|---|---|---|---|
| Found: | 57.11% | 3.89% | 5.38% | 12.81% | 13.90% |
| Calculated: | 57.26% | 4.00% | 5.56% | 12.74% | 14.08% |

EXAMPLE 66

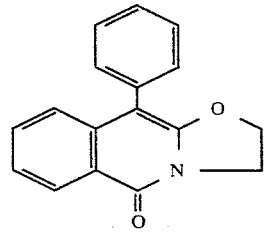

A mixture of 0.5 g. of α-phenyl-2-carboxymethylbenzoic acid, 0.14 g. of 2-aminoethanol and 3 ml. of acetic acid was refluxed for 2 hours, and then 0.4 g. of p-toluensulfonic acid was added to the reaction mixture followed by further refluxing for one hour. The reaction mixture obtained was concentrated under reduced pressure and the residue obtained was dissolved in 20 ml. of ethyl acetate, then the solution obtained was successively washed with 10 ml. of water and 10% aqueous potassium carbonate solution. The ethyl acetate solution was concentrated under reduced pressure. The residue formed was recrystallized from ethanol to provide 0.18 g. of 5-oxo-10-phenyl-2,3-dihydro-5H-oxazolo[3,2-b]isoquinoline.

Melting point 166°–168° C.

Elemental analysis for $C_{17}H_{13}NO_2$

|  | C | H | N |
|---|---|---|---|
| Found: | 77.82% | 5.31% | 4.90% |
| Calculated: | 77.55% | 4.98% | 5.32% |

EXAMPLE 67

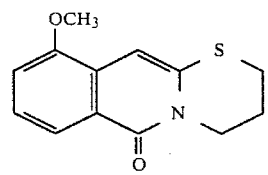

By following the same procedure as in Example 18, 10-methoxy-6-oxo-3,4-dihydro-2H,6H-1,3-thiazino[3,2-b]isoquinoline was obtained.

Melting point 117°–118° C. (recrystallized from isopropylalcohol).

EXAMPLE 68

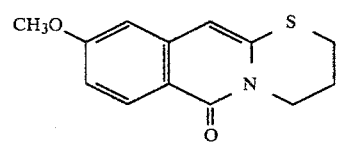

By following the same procedure as in Example 18, 9-methoxy-6-oxo-3,4-dihydro-2H,6H-1,3-thiazino[3,2-b]isoquinoline was obtained.

Melting point 86°–87° C. (recrystallized from isopropylalcohol-n-hexane).

EXAMPLE 69

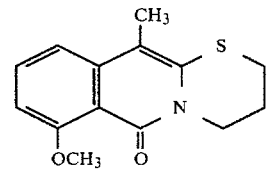

By following the same procedure as in Example 18, 11-methyl-7-methoxy-6-oxo-3,4-dihydro-2H,6H-1,3-thiazino[3,2-b]isoquinoline was obtained.

Melting point 122°–123° C. (recrystallized from cyclohexane).

EXAMPLE 70

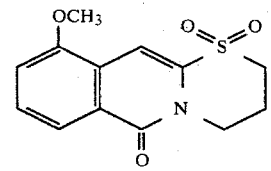

By following the same procedure as in Example 20, 10-methoxy-6-oxo-3,4-dihydro-2H,6H-1,3-thiazino[3,2-b]isoquinoline-1,1-dioxide was obtained.

Melting point 251°–252° C. (recrystallized from ethanol).

EXAMPLE 71

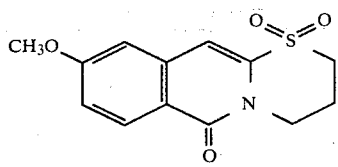

By following the same procedure as in Example 20, 9-methoxy-6-oxo-3,4-dihydro-2H,6H-1,3-thiazino[3,2-b]isoquinoline-1,1-dioxide was obtained.

Melting point 256°–257° C. (recrystallized from acetic acid).

EXAMPLE 72

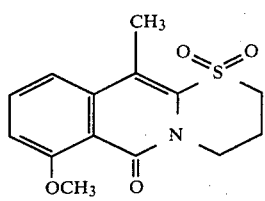

By following the same procedure as in Example 20, 11-methyl-7-methoxy-6-oxo-3,4-dihydro-2H,6H-1,3-thiazino[3,2-b]isoquinoline-1,1-dioxide was obtained.

Melting point 198°–199° C. (recrystallized from isopropylalcohol).

EXAMPLE 73

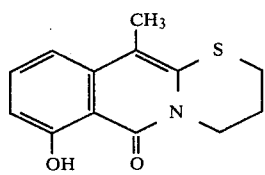

By following the same procedure as in Example 24, 7-hydroxy-11-methyl-6-oxo-3,4-dihydro-2H,6H-1,3-thiazino[3,2-b]isoquinoline was obtained.

Melting point 110°–112° C. (recrystallized from isopropylalcohol).

EXAMPLE 74

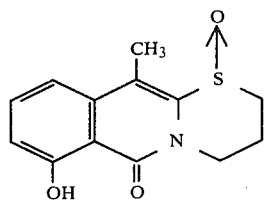

By following the same procedure as in Example 20, 7-hydroxy-11-methyl-6-oxo-3,4-dihydro-2H,6H-1,3-thiazino[3,2-b]isoquinoline-1-oxide was obtained.

Melting point 169°–170° C. (recrystallized from isopropylalcohol).

What is claimed is:

1. Nitrogen-containing heterocyclic compounds represented by the formula

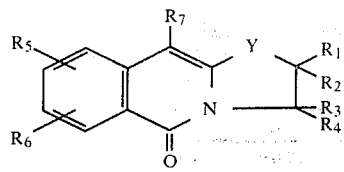

wherein Y represents

wherein m is 1 or 2; $R_1$ and $R_4$, which may be the same or different, each represents a hydrogen atom, a lower alkyl group, or a lower alkenyl group; $R_2$ and $R_3$, which may be the same or different, each represents a hydrogen atom, a hydroxyl group, a lower alkanoyloxy group, a lower alkyl group or a lower alkenyl group; said $R_2$ and $R_3$ may further form together a double bond; $R_5$ and $R_6$, which may be the same or different, each represents a hydrogen atom, a halogen atom, a hydroxyl group, a nitro group, an amino group, a lower alkoxy group, a mono or di lower alkylamino group, or a lower alkyl group; said $R_5$ and $R_6$ may further form together a lower alkylenedioxy group; and $R_7$ represents a hydrogen atom, a halogen atom, a lower alkanoyl group, a phenyl group, a phenyl lower alkyl group, a lower alkyl group, a hydroxy lower alkyl group, a di-lower alkylamino lower alkyl group, a pyrrolidino lower alkyl group, a piperidino lower alkyl group, a morpholine lower alkyl group, or a 4-lower alkyl-piperazino lower alkyl group; and the pharmacologically acceptable non-toxic salts thereof.

2. The compounds as claimed in claim 1 wherein $R_2$ and $R_3$ are a hydrogen atom or a lower alkyl group, and the pharmacologically acceptable non-toxic salts thereof.

3. A compound as claimed in claim 1 which is 7-chloro-5-oxo-2,3-dihydro-5H-thiazolo[3,2-b]isoquinoline-1-oxide and the pharmacologically acceptable non-toxic salts thereof.

4. A compound as claimed in claim 1 which is 7-chloro-3-methyl-5-oxo-2,3-dihydro-5H-thiazolo[3,2-b]isoquinoline-1-oxide and the pharmacologically acceptable non-toxic salts thereof.

5. The compound as claimed in claim 1 wherein $R_2$ and $R_3$ are a hydrogen atom or a lower alkyl group, and $R_5$ or $R_6$ is a halogen atom.

6. The compound as claimed in claim 1 wherein $R_2$ and $R_3$ are a hydrogen atom or a lower alkyl group, and $R_5$ or $R_6$ is a mono or di lower alkylamino group.

7. A compound as claimed in claim 1 which is 5-oxo-2,3-dihydro-5H-thiazolo[3,2-b]isoquinoline-1-oxide and the pharmacologically acceptable non-toxic salts thereof.

8. A compound as claimed in claim 1 which is 5-oxo-5H-thiazolo[3,2-b]isoquinoline-1,1-dioxide and the pharmacologically acceptable non-toxic salts thereof.

9. A compound as claimed in claim 2 which is 5-oxo-2,3-dihydro-5H-thiazolo[3,2-b]isoquinoline-1,1-dioxide and the pharmacologically acceptable non-toxic salts thereof.

10. A compound as claimed in claim 5 which is 7-chloro-5-oxo-2,3-dihydro-5H-triazolo[3,2-b]isoquinoline-1,1-dioxide and the pharmacologically acceptable non-toxic salts thereof.

11. A compound as claimed in claim 5 which is 7-chloro-3-methyl-5-oxo-2,3-dihydro-5H-thiazolo[3,2-b]isoquinoline-1,1-dioxide and the pharmacologically acceptable non-toxic salts thereof.

12. A compound as claimed in claim 6 which is 7-dimethylamino-5-oxo-2,3-dihydro-5H-thiazolo[3,2-b]isoquinoline-1-oxide and the pharmacologically acceptable non-toxic salts thereof.

13. A compound as claimed in claim 5 which is 7-chloro-5-oxo-5H-thiazolo[3,2-b]isoquinoline-1,1-dioxide and the pharmacologically acceptable non-toxic salts thereof.

14. An analgesic antiinflammatory composition which contains a therapeutically effective amount of the compound of claim 1 and a pharmacologically acceptable diluent.

15. The pharmaceutical composition as claimed in claim 14 which contains 7-chloro-5-oxo-2,3-dihydro-5H-thiazolo[3,2-b]isoquinoline-1-oxide and a pharmacologically acceptable diluent.

16. The pharmaceutical composition as claimed in claim 14 which contains 7-chloro-3-methyl-5-oxo-2,3-dihydro-5H-thiazolo[3,2-b]isoquinoline-1-oxide and a pharmacologically acceptable diluent.

17. A method of producing strong analgesic antiinflammatory activity which comprises administering to a host an effective amount of a compound of claim 1.

* * * * *